United States Patent
Cole et al.

(10) Patent No.: US 12,290,451 B2
(45) Date of Patent: May 6, 2025

(54) APPARATUS AND METHOD FOR EVALUATING KNEE GEOMETRY

(71) Applicant: Little Engine, LLC, Belmont, NC (US)

(72) Inventors: J. Dean Cole, Orlando, FL (US); Franz W. Kellar, Gastonia, NC (US); Michael D. Bissette, Belmont, NC (US); Franz Austen Kellar, Gastonia, NC (US); Harold L. Crowder, Concord, NC (US)

(73) Assignee: DYNAMIC BALANCER SYSTEMS LLC, Belmont, NC (US)

( * ) Notice: Subject to any disclaimer, the term of this patent is extended or adjusted under 35 U.S.C. 154(b) by 339 days.

(21) Appl. No.: 17/689,008

(22) Filed: Mar. 8, 2022

(65) Prior Publication Data
US 2022/0183859 A1    Jun. 16, 2022

Related U.S. Application Data

(63) Continuation of application No. 17/145,326, filed on Jan. 9, 2021, now Pat. No. 11,298,246.

(Continued)

(51) Int. Cl.
  *A61F 2/46*    (2006.01)
  *A61B 5/00*    (2006.01)
  (Continued)

(52) U.S. Cl.
  CPC .......... *A61F 2/4657* (2013.01); *A61B 5/4533* (2013.01); *A61B 5/4585* (2013.01); *A61B 34/10* (2016.02); *A61B 34/20* (2016.02); *A61F 2/461* (2013.01); *G01L 5/16* (2013.01); *G16H 10/60* (2018.01); *G16H 20/40* (2018.01); *G16H 40/20* (2018.01); *G16H 40/67* (2018.01);
  (Continued)

(58) Field of Classification Search
  CPC ...... A61F 2/461; A61B 5/4585; A61B 5/4533
  See application file for complete search history.

(56) References Cited

U.S. PATENT DOCUMENTS 6,205,411 B1    3/2001    DiGioia, III et al.
7,849,751 B2    12/2010   Clark et al.
(Continued)

OTHER PUBLICATIONS

International Search Report and Written Opinion issued on Sep. 10, 2021 for corresponding International Patent Application No. PCT/US2021/031961.

*Primary Examiner* — Andrew Yang
(74) *Attorney, Agent, or Firm* — Shumaker, Loop & Kendrick, LLP; Jonathan M. Hines

(57) ABSTRACT

A method of evaluating a human knee joint which includes a femur bone, a tibia bone, a patella bone, a patellar tendon, and ligaments, wherein the ligaments and patellar tendon are under anatomical tension to connect the femur and tibia together, creating a load-bearing articulating joint, the method including: inserting into the knee joint a gap balancer that includes a tibial interface surface, an opposed femoral interface surface, and at least one force sensor, the method including: providing an electronic receiving device; moving the knee joint through at least a portion of its range of motion; while moving the knee joint, using the electronic receiving device to collect data from the at least one force sensor; processing the collected data to produce a digital geometric model of at least a portion of the knee joint; and storing the digital geometric model for further use.

10 Claims, 41 Drawing Sheets

Related U.S. Application Data

(60) Provisional application No. 63/027,101, filed on May 19, 2020.

(51) Int. Cl.

| | | |
|---|---|---|
| *A61B 34/10* | (2016.01) | |
| *A61B 34/20* | (2016.01) | |
| *G01L 5/16* | (2020.01) | |
| *G16H 10/60* | (2018.01) | |
| *G16H 20/40* | (2018.01) | |
| *G16H 40/20* | (2018.01) | |
| *G16H 40/67* | (2018.01) | |
| *G16H 50/20* | (2018.01) | |
| *A61B 17/02* | (2006.01) | |
| *A61B 34/00* | (2016.01) | |
| *A61B 90/00* | (2016.01) | |

(52) U.S. Cl.
CPC ............ *G16H 50/20* (2018.01); *A61B 5/6847* (2013.01); *A61B 2017/0268* (2013.01); *A61B 2034/105* (2016.02); *A61B 2034/256* (2016.02); *A61B 2090/064* (2016.02); *A61B 2090/3983* (2016.02); *A61F 2002/4633* (2013.01); *A61F 2002/4666* (2013.01)

(56) References Cited

U.S. PATENT DOCUMENTS

| | | |
|---|---|---|
| 9,585,615 B2 | 3/2017 | Singh et al. |
| 2004/0064191 A1 | 4/2004 | Wasielewski |
| 2009/0299483 A1 | 12/2009 | Amirouche et al. |
| 2010/0249659 A1 | 9/2010 | Sgerman et al. |
| 2014/0277526 A1 | 9/2014 | Stein et al. |
| 2018/0185100 A1 | 7/2018 | Weinstein et al. |

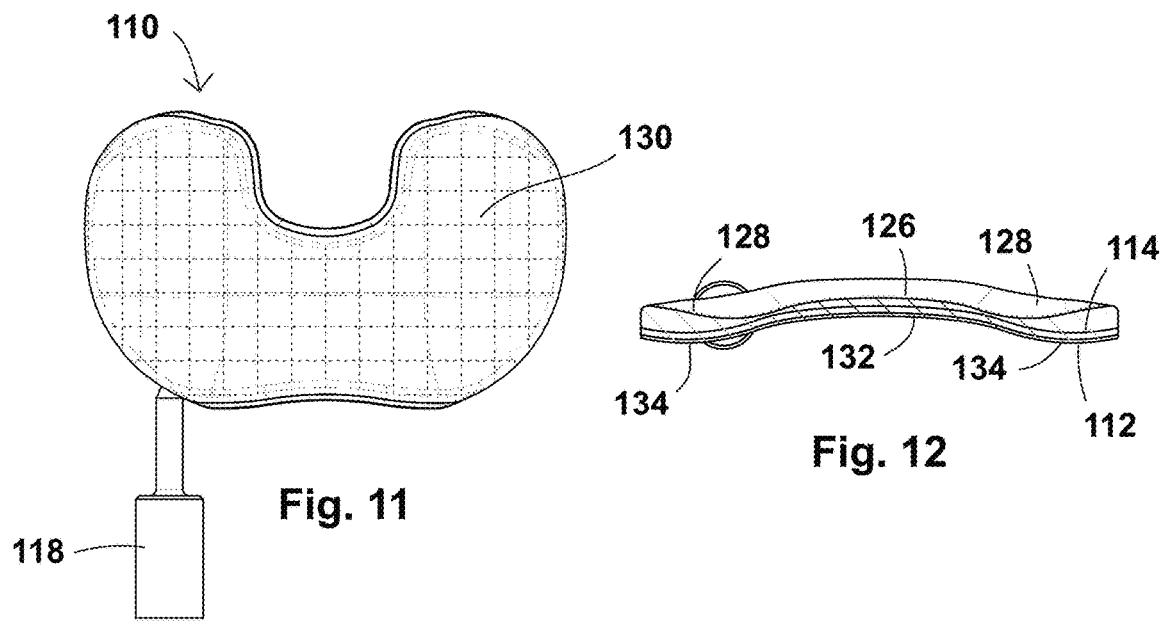
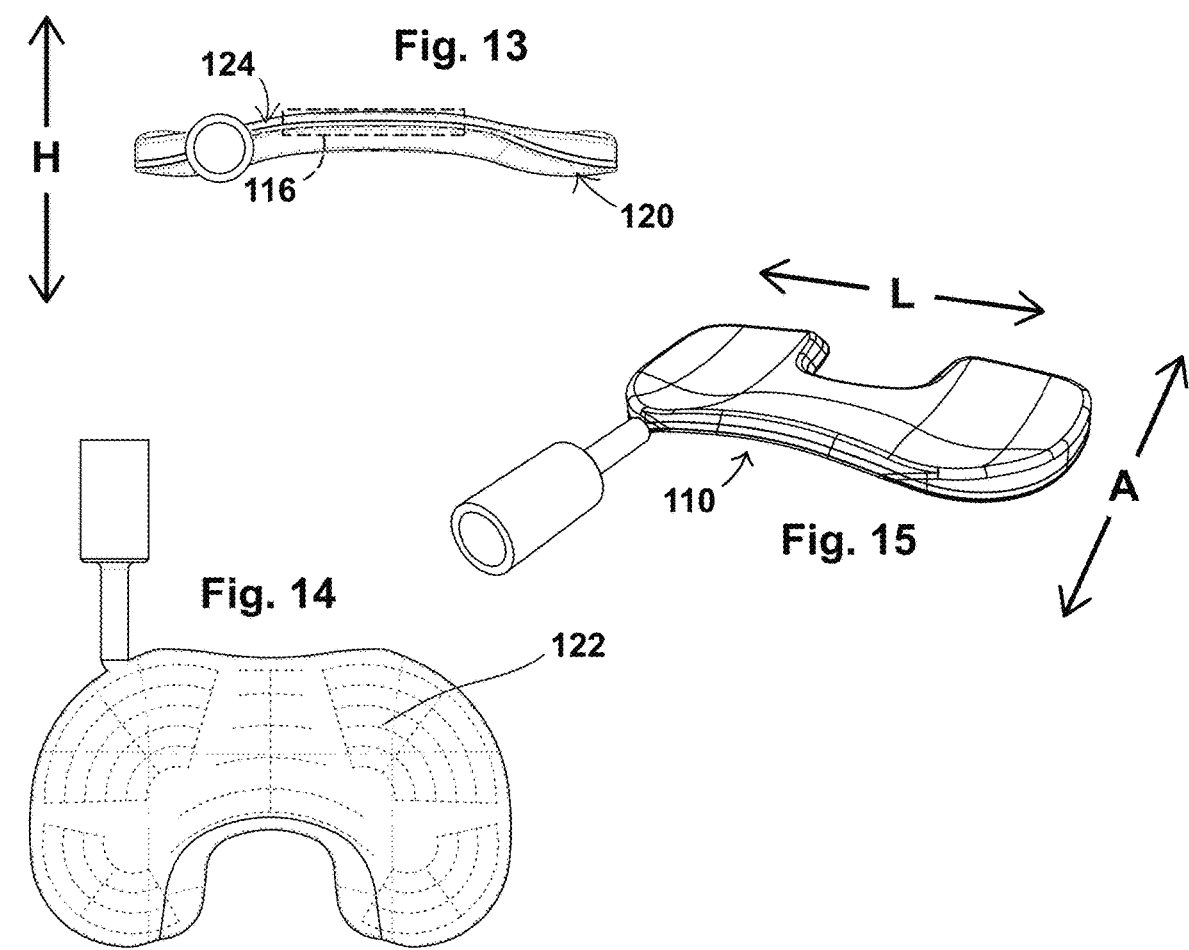

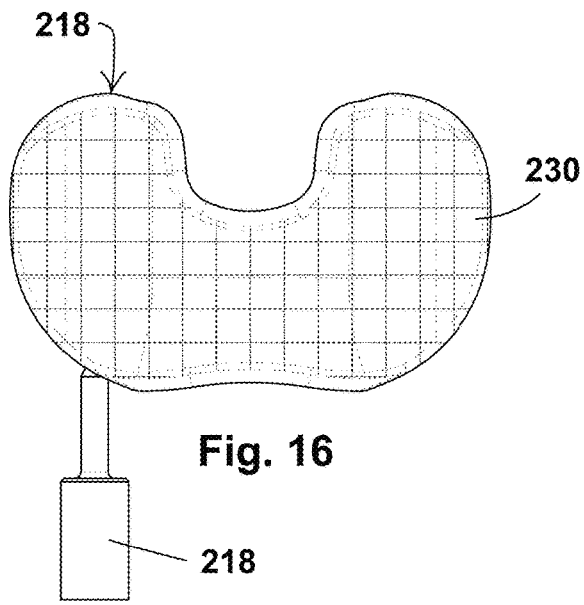
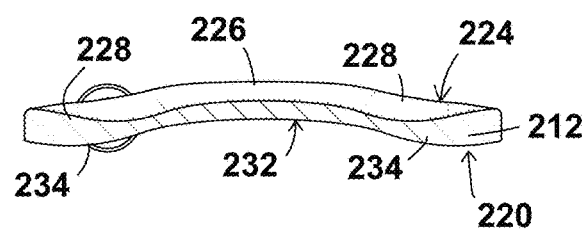
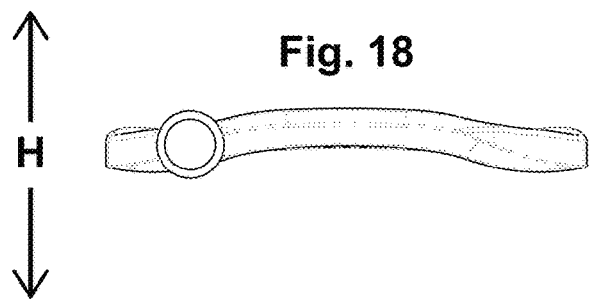
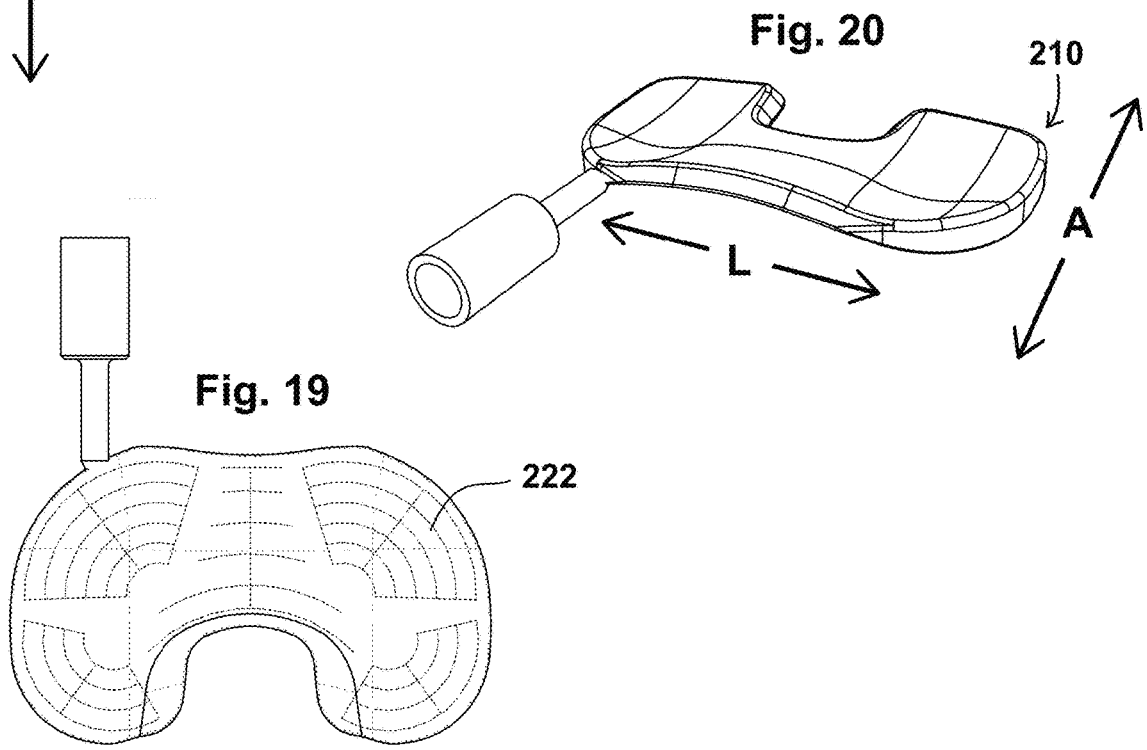

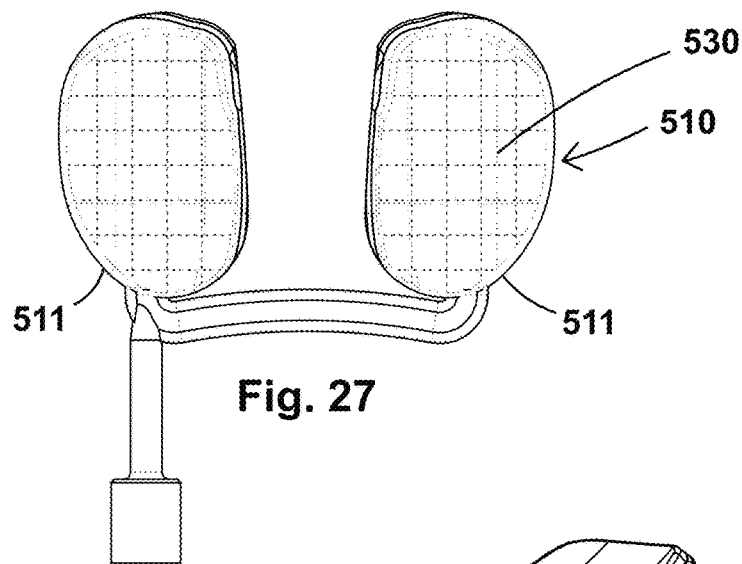
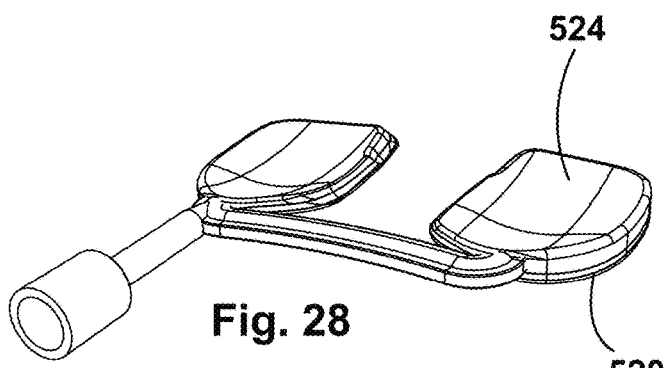
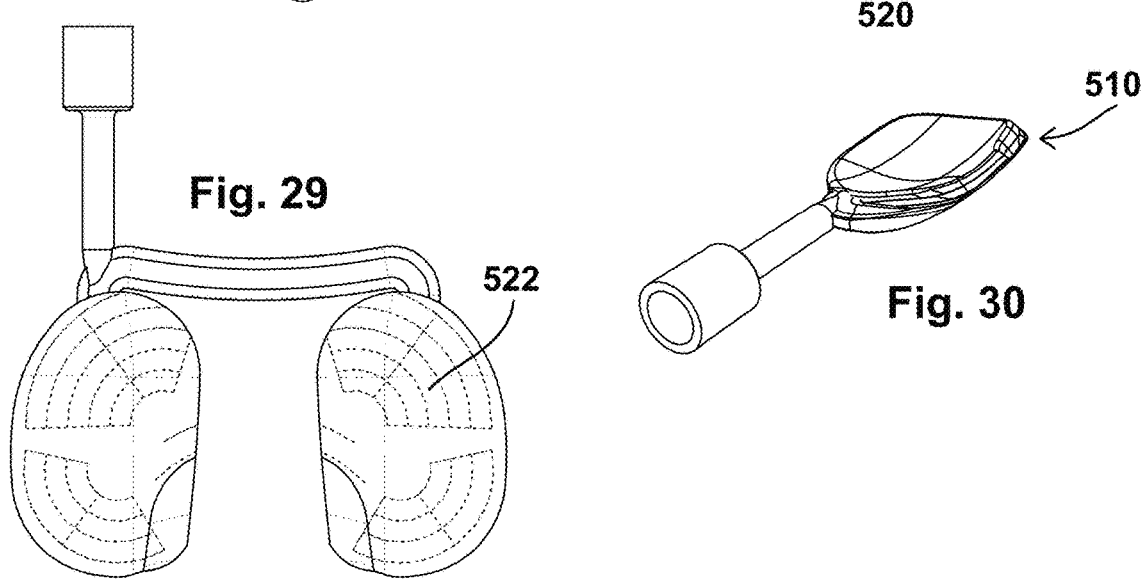

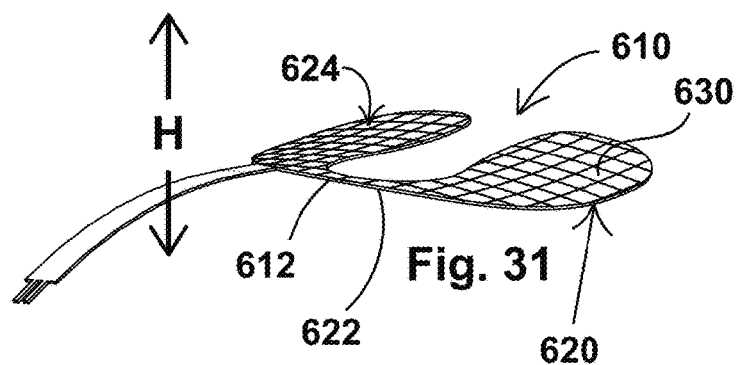
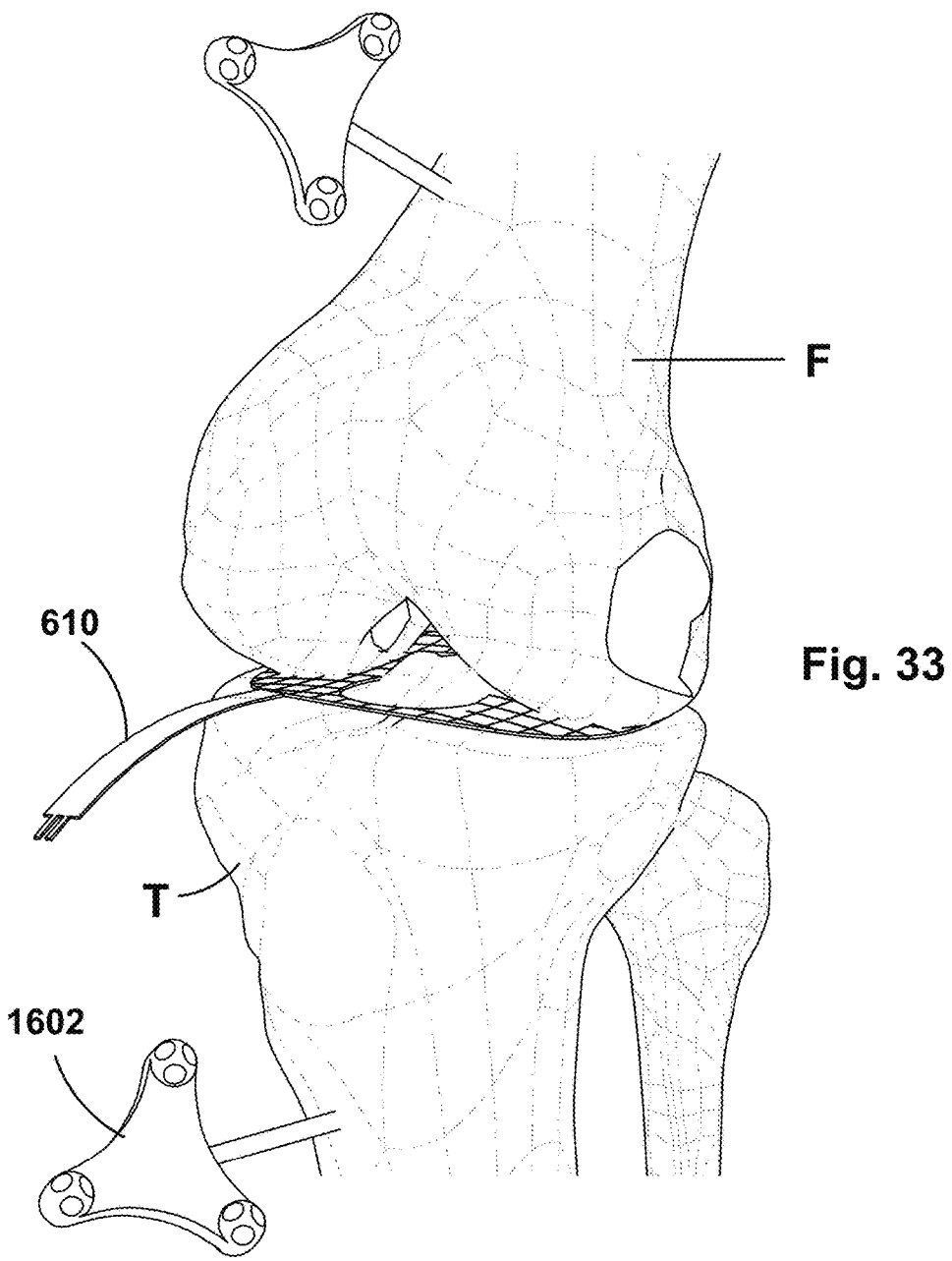

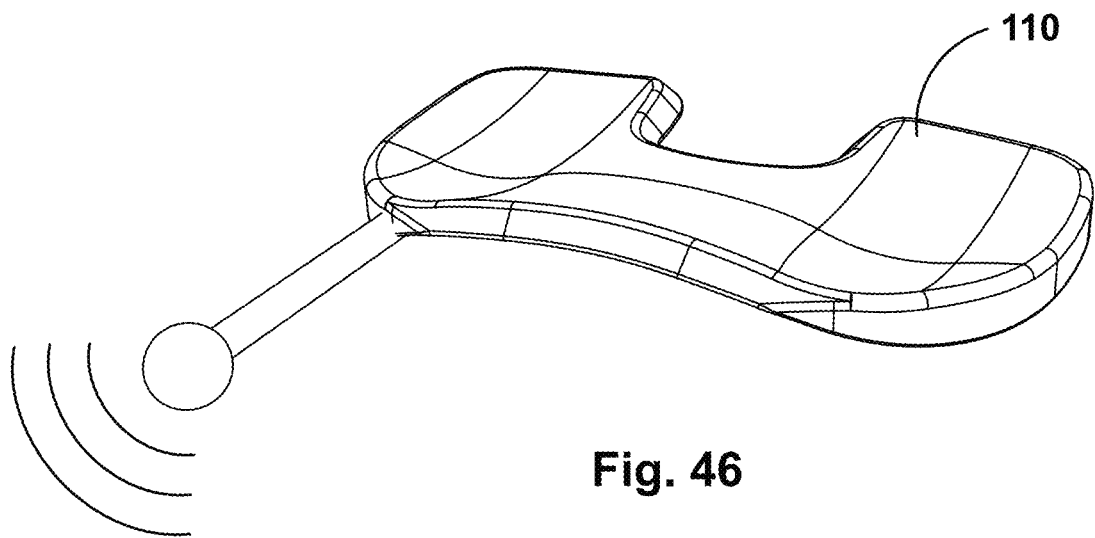
Fig. 46
Fig. 47
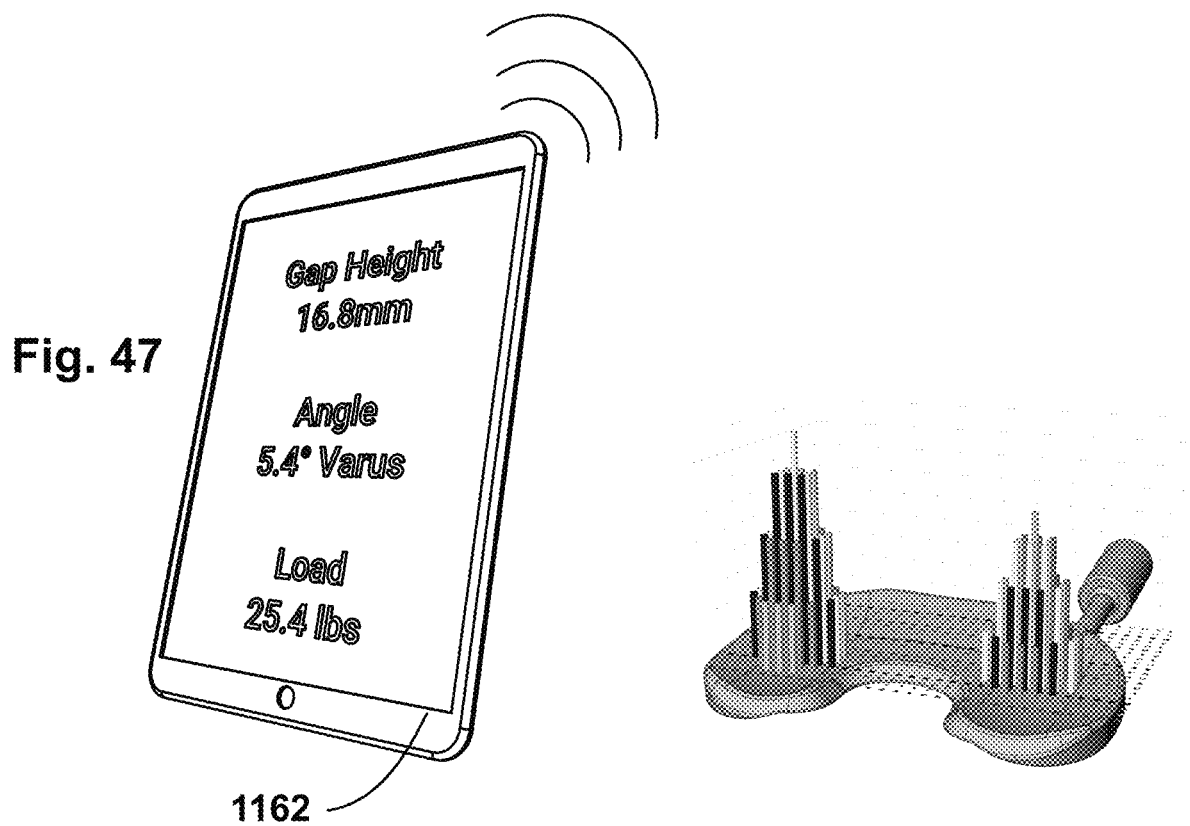
Fig. 48

APPARATUS AND METHOD FOR EVALUATING KNEE GEOMETRY

BACKGROUND

This invention relates generally to medical devices and instruments, and more particularly to a method for evaluating the geometry of a human knee joint in order to facilitate repair, augment, or replacement.

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal femoral cut 2 cooperate to define an extension gap "EG". FIGS. 3 and 4 show the joint J in flexion, with a cutting plane 3 shown for a posterior cut. The tibial cut 1 and the posterior cut 3 cooperate to define a flexion gap "FG".

A goal of total knee arthroplasty is to obtain symmetric and balanced flexion and extension gaps FG, EG (in other words, two congruent rectangles). These gaps are generally measured in millimeters of separation, are further characterized by a varus or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side or have a surgeon-selected relationship, and in each position.

Some surgeons favor the use of a measured resection technique in which bone landmarks, such as the trans epicondylar, the anterior-posterior, or the posterior condylar axes are used to determine proper femoral component rotation and subsequent gap balance. Others favor a "gap balancing technique" in which the femoral component is positioned parallel to the resected proximal tibia with each collateral ligament substantially equally tensioned or tensioned with a surgeon-selected relationship to obtain a rectangular flexion gap.

Gap balancing may be better understood by considering the characteristics of the human knee joint, particularly of the soft tissue (e.g., ligaments). FIG. 5 is a representative diagram of knee joint gap height versus applied extension load, similar to a stress-strain plot. In FIG. 5, the solid line is representative of properties of a perfectly elastic member (e.g., a rubber band). The dashed line is representative of the properties of a hypothetical infinitely rigid member. The dotted line is representative of the properties of a human knee joint ligament. It can be seen that the ligament is quite stiff and exhibits a low elongation to failure. The vertical portion of the dotted line indicates the range of motion where a minimal applied load will take up all available slack in the ligament. The slope of the gap height/load curve then rapidly transitions through the arcuate corner in the dotted line, to a very rigid characteristic. Given these properties, it will be apparent that the application of a relatively small load will ensure that the ligament is at full extension. In one example, an extension load of about 300 N or less may be applied. It will be understood that the chart in FIG. 5 is general in nature, and that specific ligaments in specific joints may have different magnitudes of slack available, or stated another way, the length of the vertical segment of the dotted line will vary from joint to joint and ligament to ligament. For example, in one patient's knee joint, all slack may be taken up at a relatively small gap height such as 9.5 mm. In another patient's knee joint, all slack may be taken up at a relatively larger height such as 20 mm.

One problem with prior art balancing techniques is that it is difficult and complex to achieve the proper balance. Current state-of-the-art gap balancing devices do not enable balancing with the patella in-place and are large, overly-complicated devices that work only with their respective knee systems They also cannot measure ligament tension throughout the range of knee motion.

BRIEF SUMMARY OF THE INVENTION

This problem is addressed by a using gap balancer (also referred to as a tensioner-balancer, distractor, or distractor-tensioner) operable to measure characteristics of the joint such as a gap distance, angle between the bones, loads, and/or deflections, and optionally to apply a load to a gap between the bones of a joint (i.e., distract the joint).

According to one aspect of the technology described herein, a method is provided of evaluating a human knee joint which includes a femur bone, a tibia bone, a patella bone, and ligaments, wherein the ligaments are under anatomical tension to connect the femur and tibia together, creating a load-bearing articulating joint, the method including: inserting into the knee joint a gap balancer that includes a tibial interface surface, an opposed femoral interface surface, and at least one force sensor; providing an electronic receiving device; moving the knee joint through at least a portion of its range of motion; while moving the knee joint, using the electronic receiving device to collect data from the at least one force sensor; processing the collected data to produce a digital geometric model of at least a portion of the knee joint; and storing the digital geometric model for further use.

According to another aspect of the technology described herein, a gap balancer for evaluating a human knee joint includes: a body including a tibial interface surface, an opposed femoral interface surface, and at least one force sensor, wherein the force sensor has at least a two-axis array resolution.

According to another aspect of the technology described herein, a method is provided of evaluating a human knee joint which includes a femur bone, a tibia bone, a patella bone, and ligaments, wherein the ligaments are under anatomical tension to connect the femur and tibia together, creating a load-bearing articulating joint, the method including: without making a tibial plateau cut, inserting into the knee joint a gap balancer that includes a tibial interface surface, an opposed femoral interface surface, and at least one force sensor, wherein the force sensor has at least a two-axis array resolution, with the gap balancer in a retracted position; moving the gap balancer towards an extended position, so as to urge the tibia and the femur apart and apply tension to ligaments of the knee joint; providing an electronic receiving device; moving the knee joint through at least a portion of its range of motion; while moving the knee joint, using the electronic receiving device to collect data from the at least one force sensor; processing the collected data to produce a digital geometric model of at least a portion of the knee joint; and storing the digital geometric model for further use.

According to another aspect of the technology described herein, a gap balancer for evaluating a human knee joint includes: a body including a non-planar tibial interface surface and an opposed non-planar femoral interface surface, wherein the gap balancer is operable to move between a retracted position and an extended position so as to distract the knee joint; and at least one force sensor, wherein the force sensor has at least a two-axis array resolution.

BRIEF DESCRIPTION OF THE DRAWINGS

The invention may be best understood by reference to the following description taken in conjunction with the accompanying drawing figures in which:

FIGS. 11-15 are schematic views of an exemplary embodiment of a gap balancer for a human knee joint;

FIGS. 16-20 are schematic views of another exemplary embodiment of a gap balancer for a human knee joint;

FIGS. 27-30 are schematic views of another exemplary embodiment of a gap balancer for a human knee joint;

FIGS. 31-33 are schematic views of another exemplary embodiment of a gap balancer for a human knee joint;

FIG. 46 is a schematic view of gap balancer having a wireless connection;

FIG. 47 is a schematic view of a receiving device in data communication with the gap balancer of FIG. 46;

FIG. 48 is a conceptual view of a graphic representation of load data;

DETAILED DESCRIPTION OF THE INVENTION

Figures 1, 2:
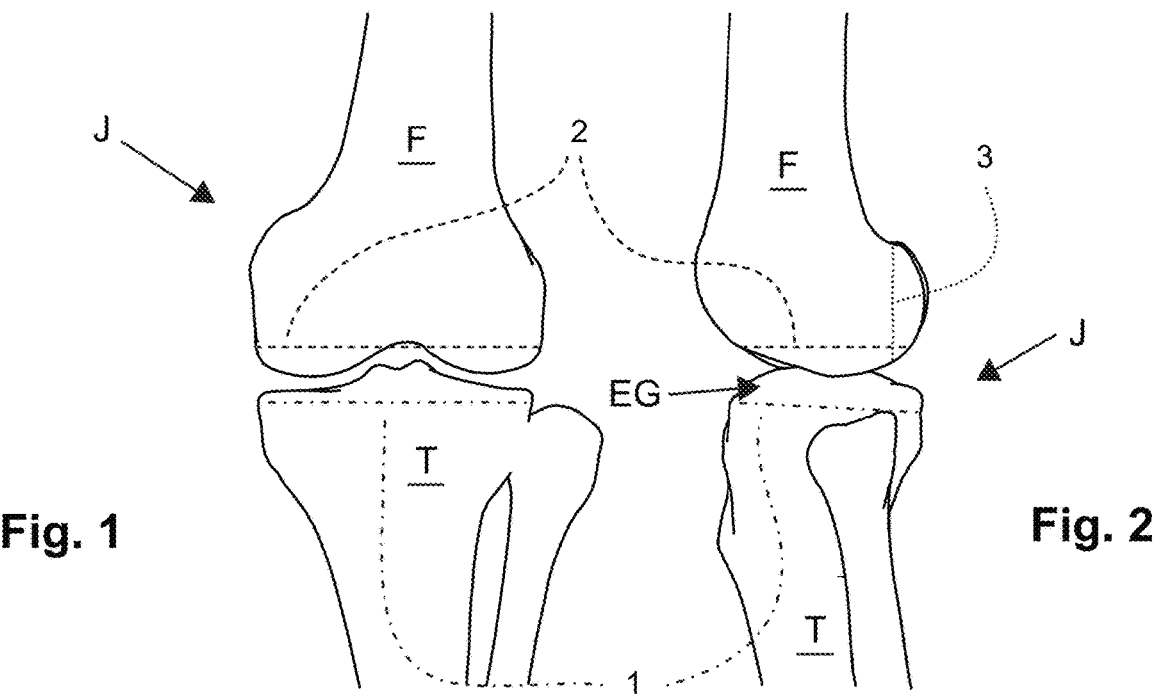
FIG. 1 is a view of the anterior aspect of the human knee joint in extension showing cutting planes for a total knee arthroscopy.
FIG. 2 is a view of the lateral aspect of the human knee joint of FIG. 1.
Figures 3, 4:
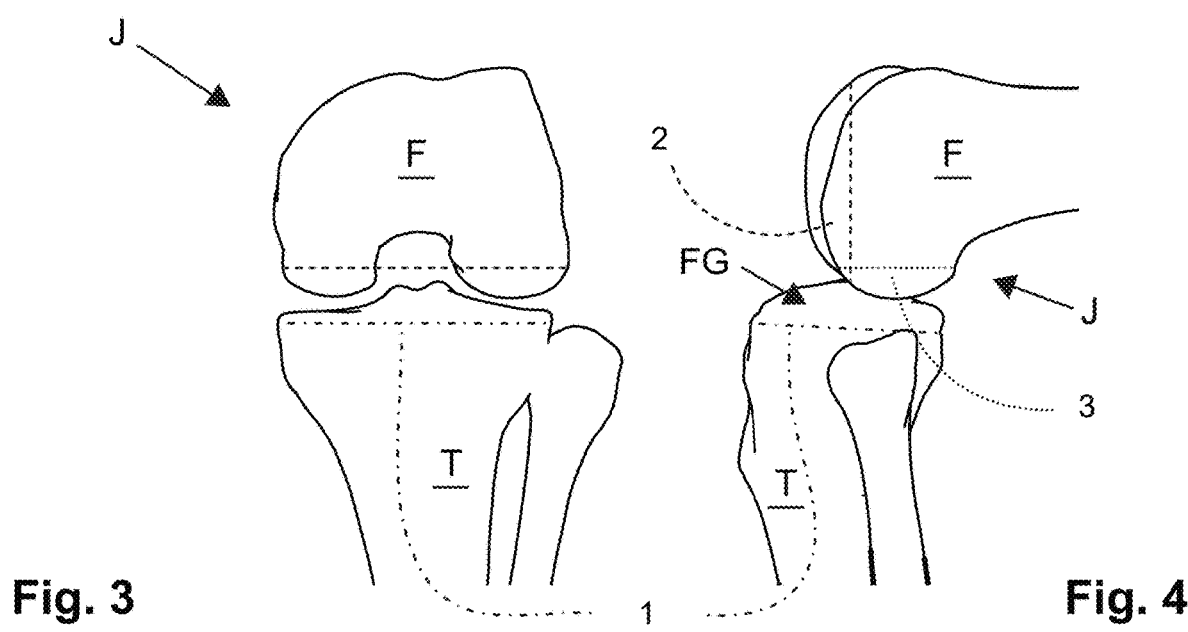
FIG. 3 is a view of the anterior aspect of the human knee joint in flexion showing cutting planes for a total knee arthroscopy.
FIG. 4 is a view of the lateral aspect of the human knee joint of FIG. 3.
Figure 5:
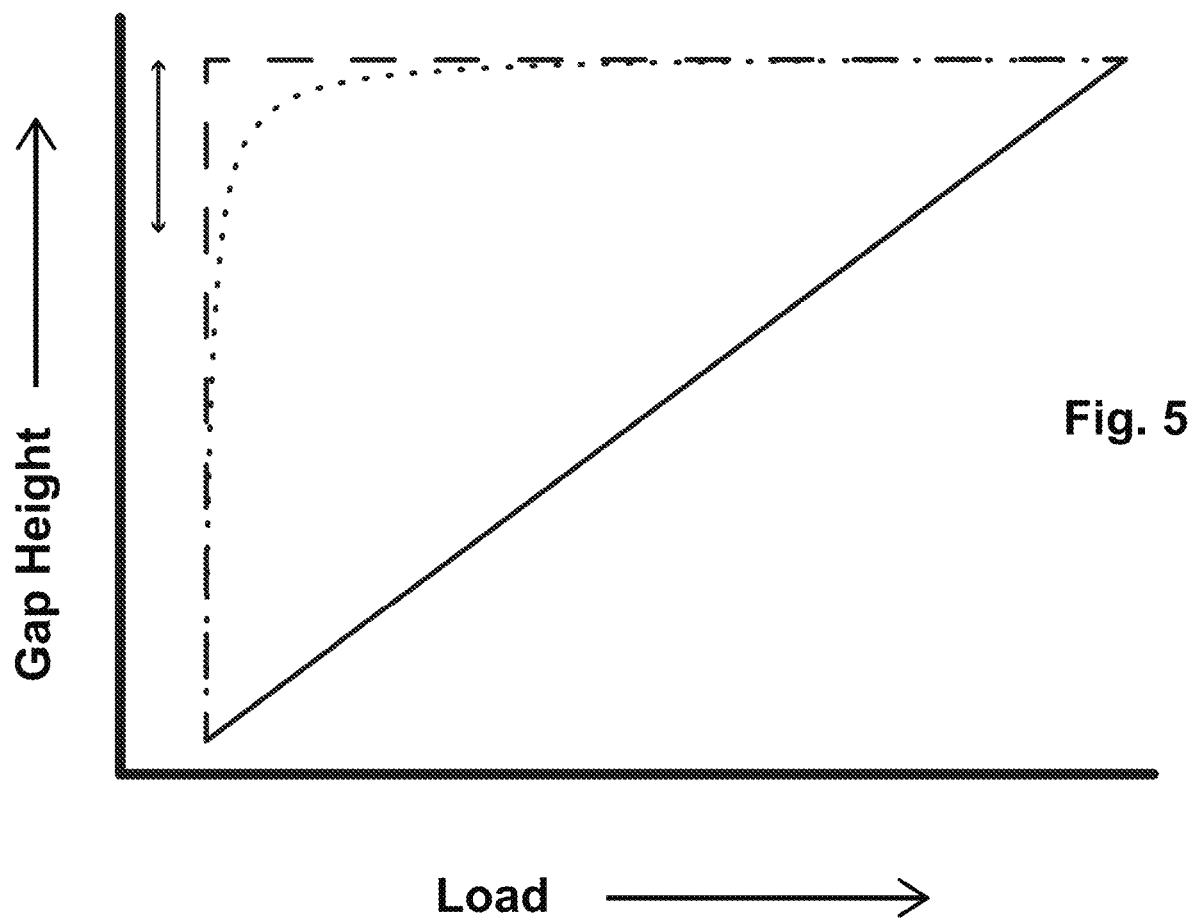
FIG. 5 is a graph illustrating the stress-strain properties of the ligaments in a human knee joint.

Now, referring to the drawings wherein identical reference numerals denote the same elements throughout the various views, FIGS. 6-10 depict an exemplary embodiment of a gap balancer 10 (alternatively referred to in various embodiments as a tensioner-balancer, distractor, distractor-tensioner, or jack) which is useful for balancing a gap in a human knee joint as part of a total knee arthroscopy and for other therapeutic procedures.

The gap balancer 10 comprises a baseplate 12 and a top plate 14 interconnected by a distractor element 16 (shown schematically). The distractor element 16 and the gap balancer 10 are movable between a retracted position in which the top plate 14 lies close to or against the baseplate 12, and an extended position in which the top plate 14 is spaced away from the baseplate 12. As described in more detail below, a means is provided to actuate the distractor element 16 in response to an actuating force in order to separate the baseplate 12 and the top plate 14 in a controllable manner. This separation enables it to extend so as to apply a load to a knee joint. Optionally, the baseplate 12 and the top plate 14 may be arranged to be pivotable relative to each other along an axis corresponding to a varus/valgus angulation of the knee, as shown by the arrow in FIG. 8.

Figure 6:
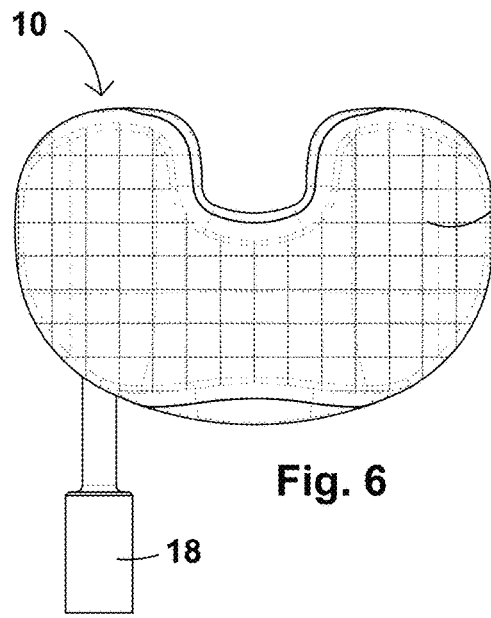
FIGS. 6-10 are schematic views of an exemplary embodiment of a gap balancer for a human knee joint.
Figure 7:
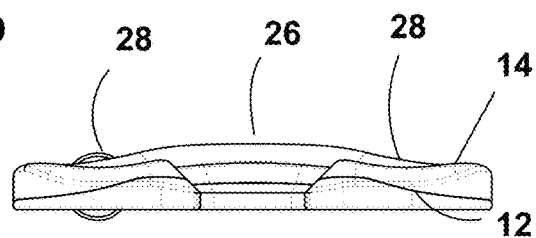
Figure 8:
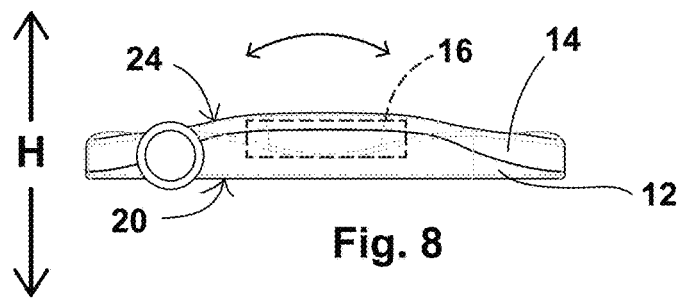
Figure 9:
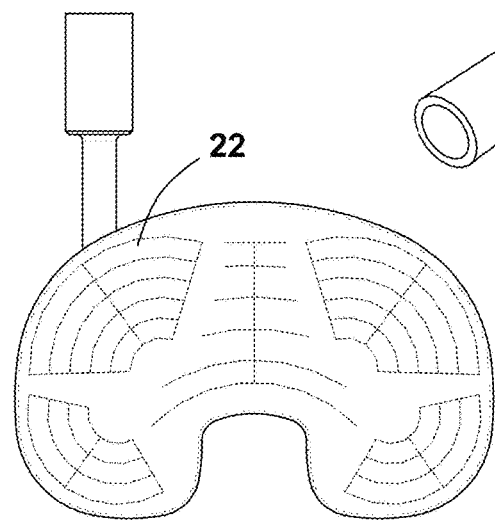
Figure 10:
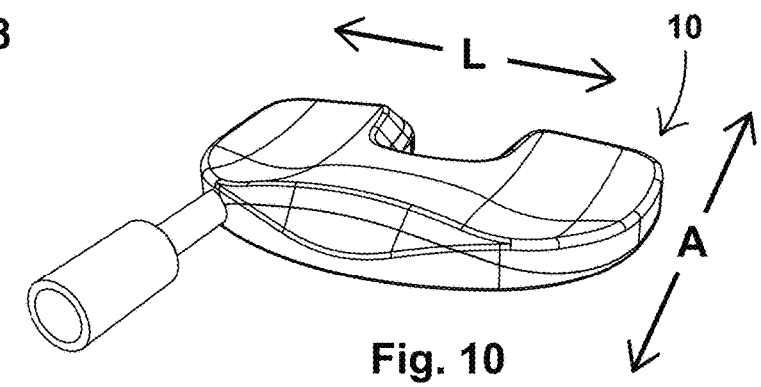

The gap balancer 10 is generally U-shaped in plan form as seen in FIG. 6. It may include a coupler 18 providing electrical, fluid, and/or mechanical connections to a controller, a receiver, or an actuating instrument as described elsewhere herein.

Solely for purposes of convenient description, the gap balancer 10 may be described as having a length extending along a lateral direction "L", a width extending along an axial direction "A", and a height or thickness extending along a vertical direction "H", wherein the lateral direction, the axial direction, and the vertical direction are three mutually perpendicular directions.

The baseplate 12 includes a generally planar tibial interface surface 20. An array of tibial force sensors 22 are attached to or integrated into the tibial interface surface 20. They may be arranged in a pattern such as a grid layout or a radial layout.

The top plate 14 includes a femoral interface surface 24. The femoral interface surface 24 is contoured to be generally conformable to the distal end of a human femur and includes a central bulge 26 flanged by a pair of concave seats 28 which are configured to receive the condyles of the human femur. An array of femoral force sensors 30 are attached to or integrated into the femoral interface surface 24. They may be arranged in a pattern such as a grid layout or a radial layout.

Each of the force sensors 22, 30 includes one or more transducers operable to detect an applied force and produce a signal representative of (e.g., proportional to) the applied force and/or pressure. Optionally, each of the force sensors 22, 30 may detect and produce a signal representative of (e.g., proportional to) displacement and/or position (e.g., height). Nonlimiting examples of transducers effective to produce a signal include strain gauges, or miniature linear variable differential transformers (LVDT), or piezoelectric transducers. The force sensors are segmented into at least a 2D or two-axis array of sensor elements, e.g., a matrix which is addressable by X, Y reference, radial coordinates, or other suitable position location. The size of the individual sensor elements in the arrays may be selected as required to produce useful and actionable information.

The sensor arrays may be connected to an electronic receiving device as described elsewhere herein by a wired or wireless connection. Appropriate processors and software may be provided for interpretation of the signals from the sensor arrays.

Generally, the overall thickness of the gap balancer 10 may be on the order of several millimeters or more. This embodiment of the device would typically be used with the baseplate 12 contacting a planar flat resected surface of the proximal end of the tibia.

FIGS. 11-15 show another embodiment of a gap balancer 110. The gap balancer 110 comprises a baseplate 112 and a top plate 114 interconnected by a distractor element 116 (shown schematically). The distractor element 116 and the gap balancer 110 are movable between a retracted position and an extended position. A means is provided to actuate the distractor element 116 in response to an actuating force in order to separate the baseplate 112 and the top plate 114 in a controllable manner. This separation enables it to extend so as to apply a load to a knee joint. As one non-limiting example, the distractor element 116 could take the form of a diaphragm which may be extended by fluid pressure.

The gap balancer 110 is generally U-shaped in plan form as seen in FIG. 11. It may include a coupler 118 providing electrical, fluid, and/or mechanical connections as described elsewhere herein.

The gap balancer 110 may be described as having a length extending along a lateral direction "L", a width extending along an axial direction "A", and a height or thickness extending along a vertical direction "H", wherein the lateral direction, the axial direction, and the vertical direction are three mutually perpendicular directions. Generally, the overall thickness of the gap balancer 110 (i.e., measured in direction H, in the retracted condition) may be on the order of one or two millimeters. In one example it may be no more than 0.75 mm thick. Unlike gap balancer 10, the gap balancer 110 could thus be inserted into a knee joint J without first having to distract the joint or cut away any tissue.

The baseplate 112 includes a tibial interface surface 120. The tibial interface surface 120 is contoured to be generally conformable to the proximal end of a human tibia and includes a central recess 132 flanged by a pair of convex bulges 134 which are configured to receive a human tibia. An array of tibial force sensors 122 of the type described above are attached to or integrated into the tibial interface surface 120. They may be arranged in a pattern such as a grid layout or a radial layout.

The top plate 114 includes a femoral interface surface 124. The femoral interface surface 124 is contoured to be generally conformable to the distal end of a human femur and includes a central bulge 126 flanged by a pair of concave seats 128 which are configured to receive the condyles of the human femur. An array of femoral force sensors 130 of the type described above are attached to or integrated into the femoral interface surface 124. They may be arranged in a pattern such as a grid layout or a radial layout.

FIGS. 16-20 show another embodiment of a gap balancer 210. The gap balancer 210 comprises a body 212 with a tibial interface surface 220 and an opposed femoral interface surface 224. The body 212 could be completely rigid or somewhat flexible, depending on the material, dimensions, and internal construction. As used herein the term "rigid" refers to being sufficiently stiff so as not to deflect appreciably under expected joint distraction loads as described elsewhere herein, whereas the term flexible refers to being able to deflect appreciably under expected joint distraction loads. The gap balancer 210 is generally U-shaped in plan form as seen in FIG. 16. It may include a coupler 218 providing electrical, fluid, and/or mechanical connections as described elsewhere herein.

The gap balancer 210 may be described as having a length extending along a lateral direction "L", a width extending along an axial direction "A", and a height or thickness extending along a vertical direction "H", wherein the lateral direction, the axial direction, and the vertical direction are three mutually perpendicular directions. Generally, the overall thickness of the gap balancer 210 (i.e., measured in direction H) may be on the order of one or two millimeters. Like gap balancer 110, the gap balancer 210 could thus be inserted into a knee joint J without first having to distract the joint or cut away any tissue. In practice, it would be used as a "wedge" to distract the knee joint by simply forcing the device into the joint. The gap balancer 210 may be provided in different thicknesses to accommodate this purpose.

The tibial interface surface 220 is contoured to be generally conformable to the proximal end of a human tibia and includes a central recess 232 flanged by a pair of convex bulges 234 which are configured to receive a human tibia. An array of tibial force sensors 222 of the type described above are attached to or integrated into the tibial interface surface 220. They may be arranged in a pattern such as a grid layout or a radial layout.

The femoral interface surface 224 is contoured to be generally conformable to the distal end of a human femur and includes a central bulge 226 flanged by a pair of concave seats 228 which are configured to receive the condyles of the human femur. An array of femoral force sensors 230 of the type described above are attached to or integrated into the femoral interface surface 224. They may be arranged in a pattern such as a grid layout or a radial layout.

FIGS. 21-24 show another embodiment of a gap balancer 310. The gap balancer 310 comprises a body 312 with a tibial interface surface 320 and an opposed femoral interface surface 324. The gap balancer 310 is generally U-shaped in plan form. It may include a coupler 318 providing electrical, fluid, and/or mechanical connections as described elsewhere herein.

Generally, the overall thickness of the gap balancer 310 (i.e., measured in direction H) may be on the order of one or two millimeters. Like gap balancer 110, the gap balancer 310 could thus be inserted into a knee joint J without first having to distract the joint or cut away any tissue.

Figure 21:
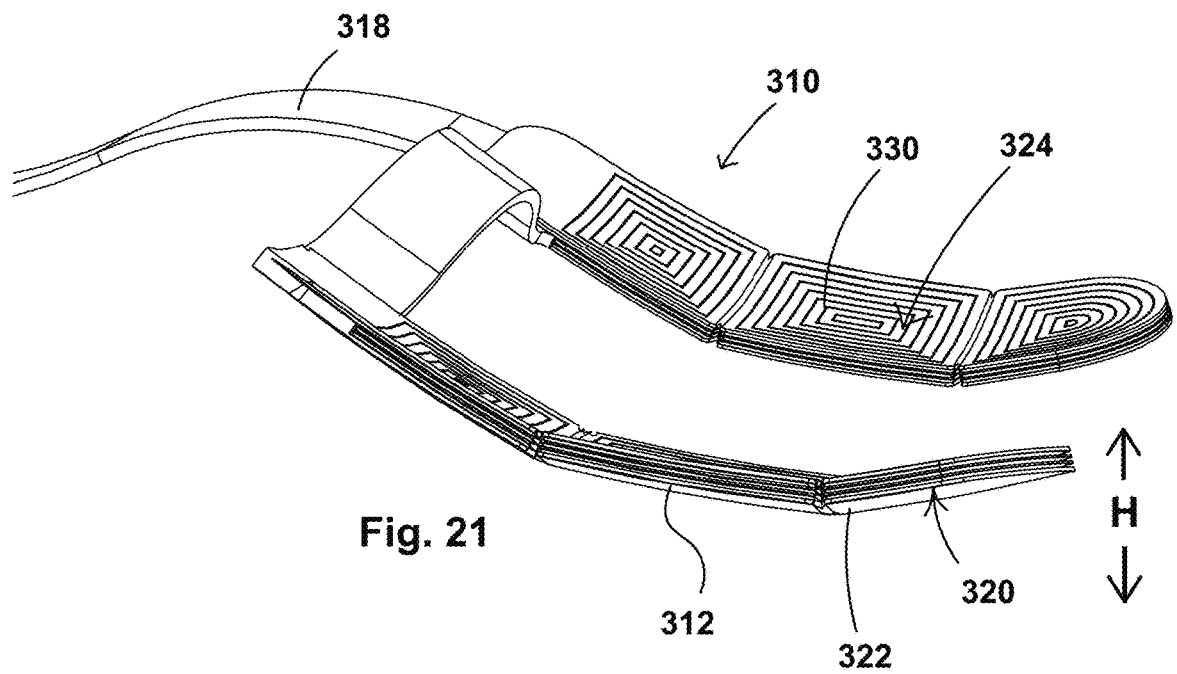
FIGS. 21-24 are schematic views of another exemplary embodiment of a gap balancer for a human knee joint.
Figure 22:
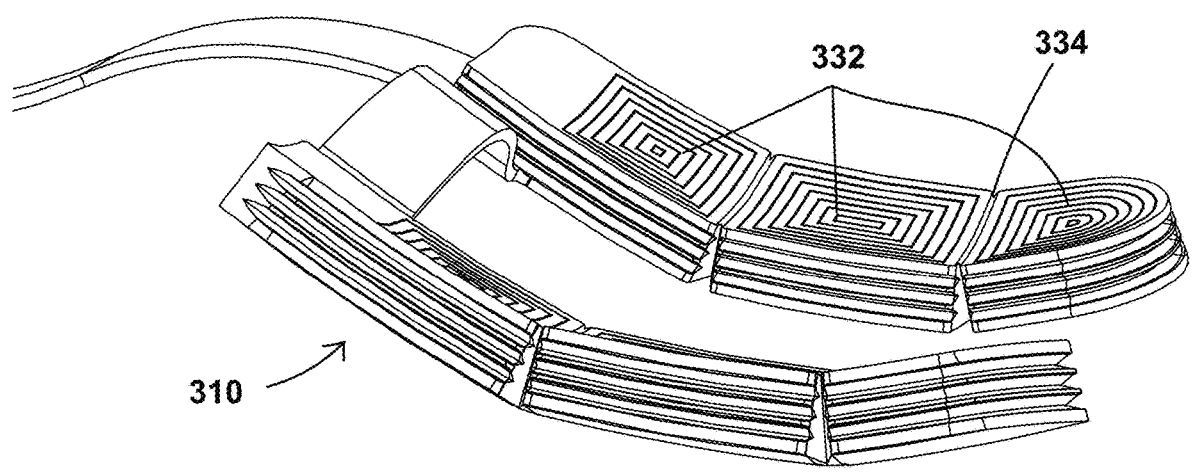
Figure 23:
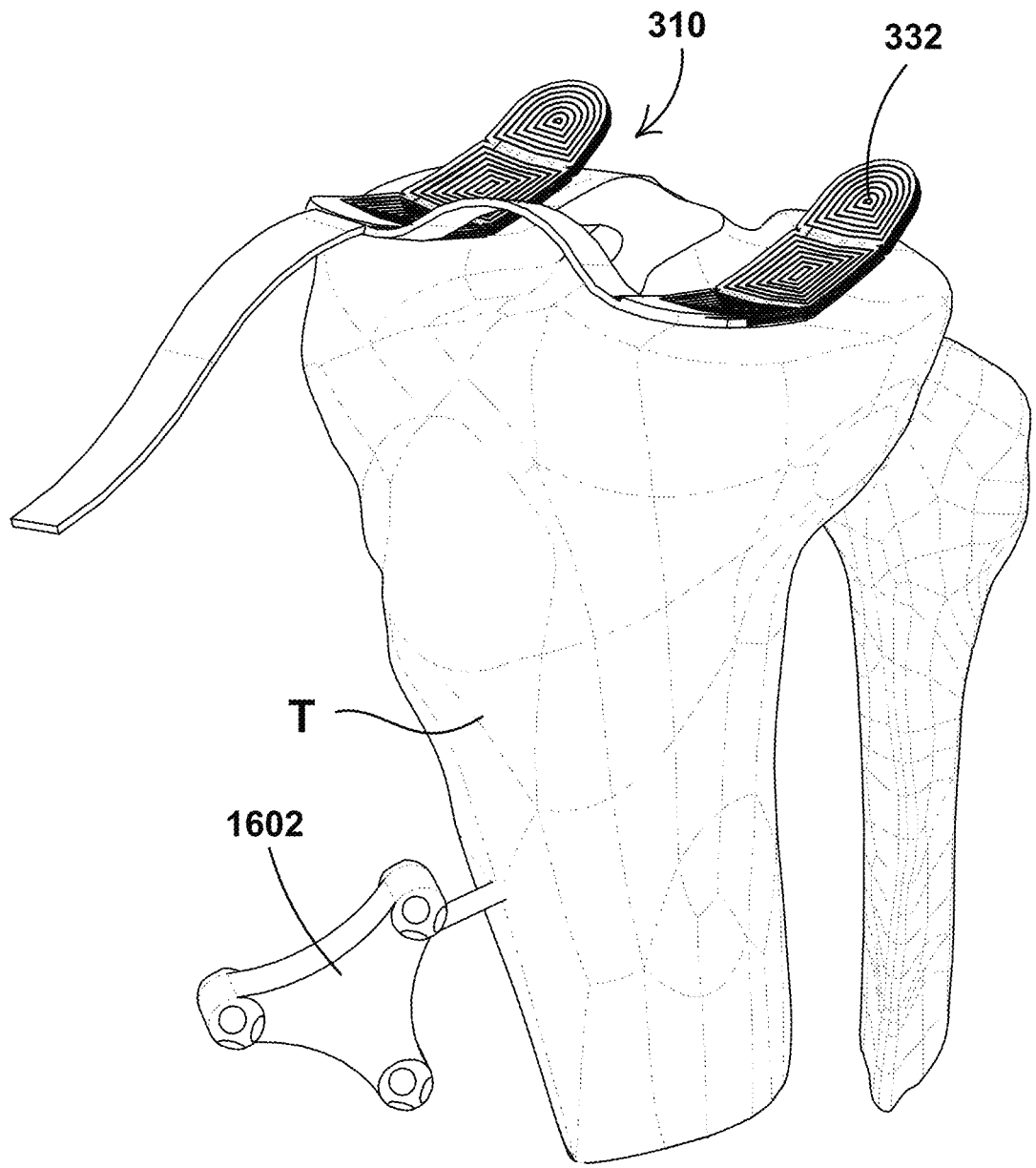
Figure 24:
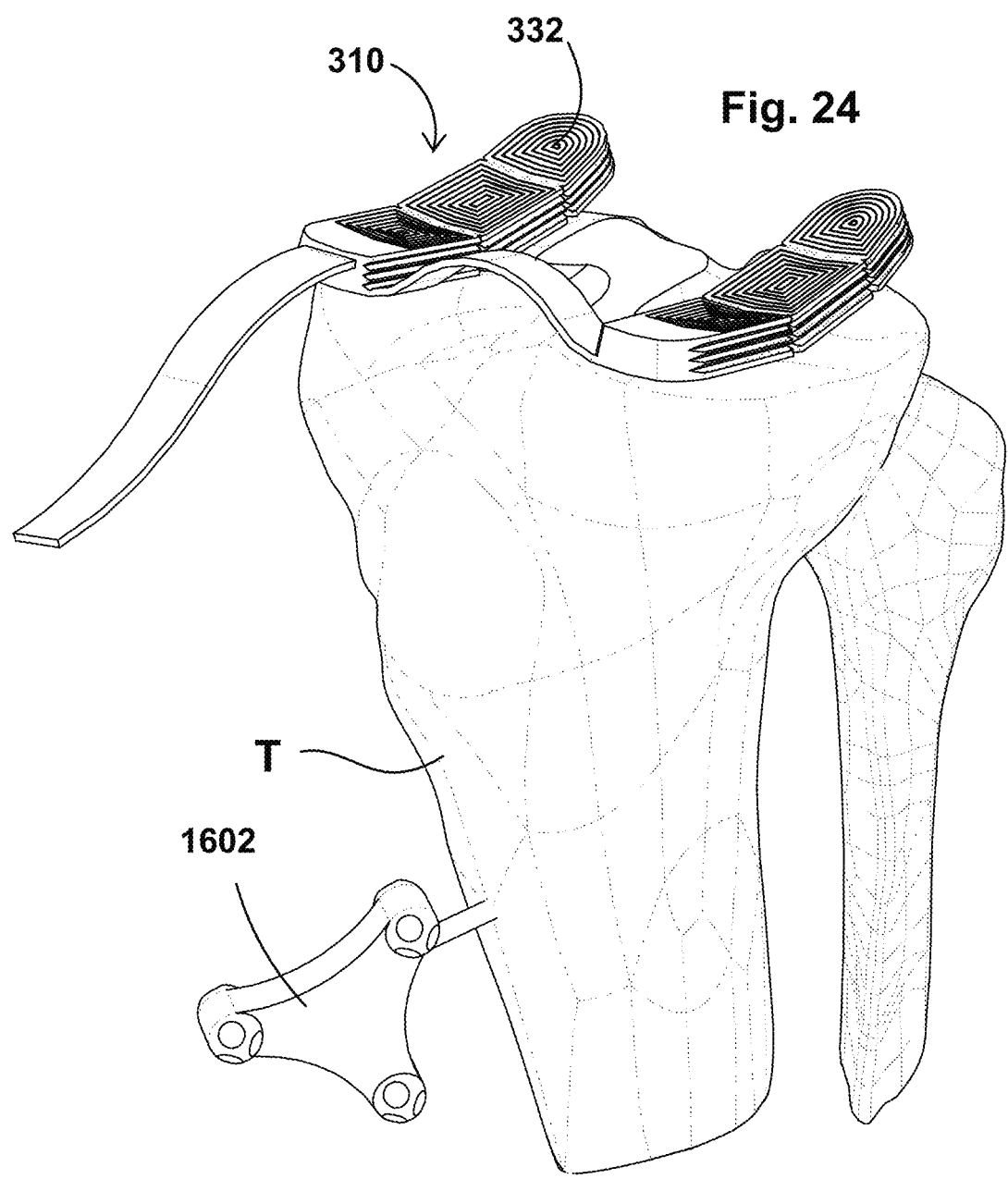

The body 312 may be divided into a plurality of segments 332 which may be hinge elements 334 (e.g., live hinge strips) to allow the segments 332 to flex or pivot relative to each other. Each of the segments 332 may take the form of an expandable hollow chamber which may be inflated by fluid pressure or other means such as discrete electromechanical actuation, for example applying an electrical charge to a superelastic or memory metal. FIG. 21 and FIG. 23 show the segments 332 in a deflated or retracted position. FIGS. 22 and 24 show the segments 332 in and inflated or extended position. The walls forming the segments 332 may be configured as an "accordion" or "corrugated" structure to permit them to selectively expand or collapse into a compact size.

An array of tibial force sensors 322 of the type described above are attached to or integrated into the tibial interface surface 320. They may be arranged in a pattern such as a grid layout or a radial layout.

An array of femoral force sensors 330 of the type described above are attached to or integrated into the femoral interface surface 324. They may be arranged in a pattern such as a grid layout or a radial layout.

Figure 25:
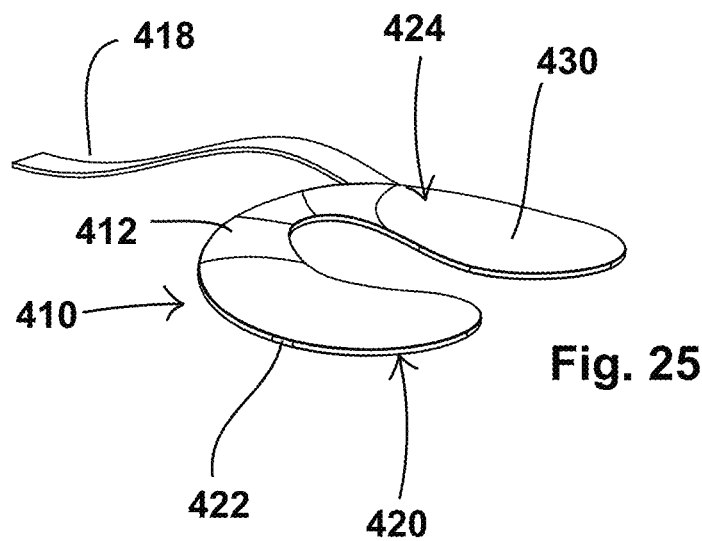
FIGS. 25 and 26 are schematic views of another exemplary embodiment of a gap balancer for a human knee joint.
Figure 26:
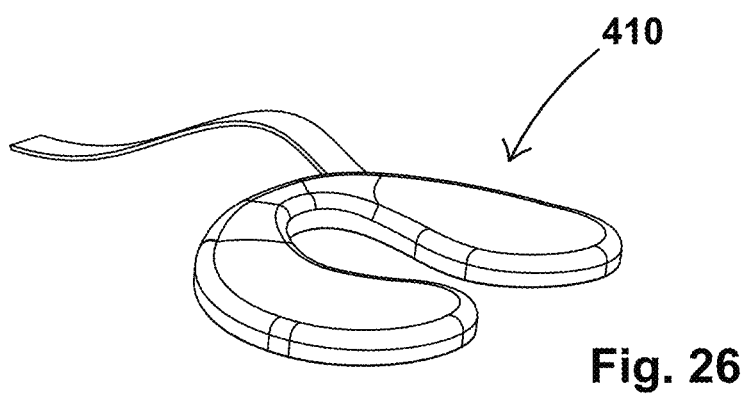

FIGS. 25 and 26 show another embodiment of a gap balancer 410. This is similar in operational principle to the gap balancer 310 described above. It comprises a body 412 with a tibial interface surface 420 and an opposed femoral interface surface 424. The primary difference between gap balancer 410 and gap balancer 310 is a gap balancer 410 does not include the individual segments for the accordion/corrugated structure. The gap balancer 410 is generally U-shaped in plan form. It may include a coupler 418 providing electrical, fluid, and/or mechanical connections as described elsewhere herein.

Generally, the overall thickness of the gap balancer 410 (i.e., measured in direction H) may be on the order of one or two millimeters. Like gap balancer 310, the gap balancer 410 could thus be inserted into a knee joint J without first having to distract the joint or cut away any tissue.

An array of tibial force sensors 422 of the type described above are attached to or integrated into the tibial interface surface 420. They may be arranged in a pattern such as a grid layout or a radial layout.

An array of femoral force sensors 430 of the type described above are attached to or integrated into the femoral interface surface 424. They may be arranged in a pattern such as a grid layout or a radial layout.

FIGS. 27-30 illustrate another exemplary gap balancer 510. This is most similar in general principle to the gap balancer 110 described above. It may be actuated for power distraction of the knee joint as described above or may be a non-extensible "wedge" device. It differs from the gap balancer 110 in that it employs two spaced-apart lobes 511, one for each condyle of the femur. Each lobe 511 includes a femoral interface surface 524 with an array of femoral sensors 530 and a tibial interface surface 520 with an array of tibial sensors 522. This device may be used without interference with the ACL or PCL of the knee joint. The gap balancer 510 of the embodiments shown in FIGS. 27-29 may be configured for one or both condyles. For example, the device of FIG. 27 could include a single lobe 511 instead of two. A complete knee replacement could be performed leaving the native ACL and/or PCL intact and/or augmented. A soft tissue balancing procedure could be carried out using either a dual-lobe device as in FIG. 27, or two single-lobe devices (item 510', FIG. 30) approaching from the medial and lateral aspects, respectively.

Figure 32:
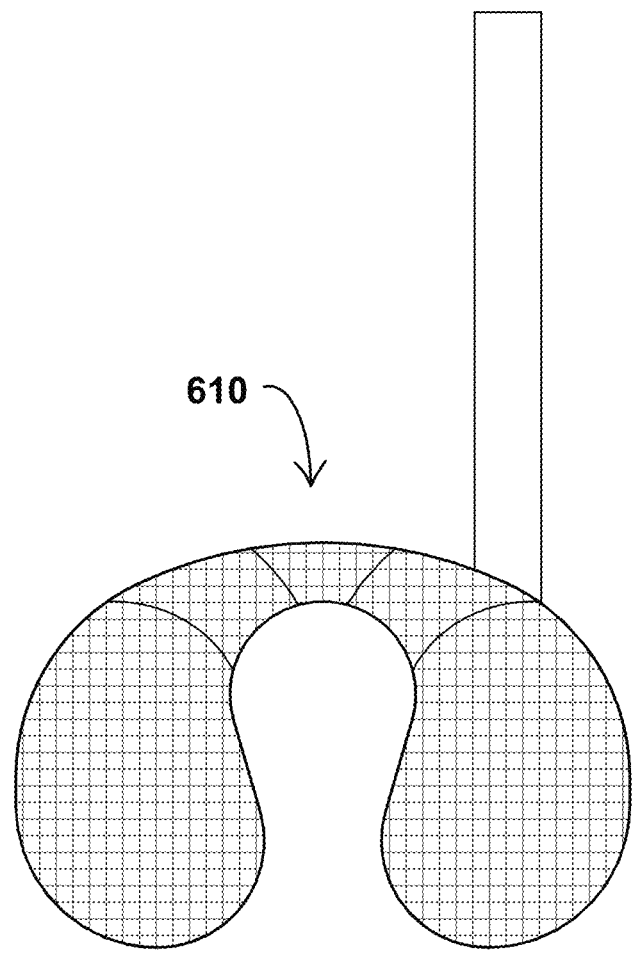

FIGS. 31-33 illustrate another embodiment of a gap balancer 610. This has a body 612 comprising a thin, membrane-like incompressible shim. The body 612 is U-shaped in plan view and has a tibial interface surface 620 and an opposed femoral interface surface 624.

Generally, the overall thickness of the gap balancer 610 (i.e., measured in direction H) may be on the order of one or two millimeters. Like gap balancer 410, the gap balancer 610 could thus be inserted into a knee joint J without first having to distract the joint or cut away any tissue.

An array of tibial force sensors 622 of the type described above are attached to or integrated into the tibial interface surface 620. They may be arranged in a pattern such as a grid layout or a radial layout.

An array of femoral force sensors 630 of the type described above are attached to or integrated into the femoral interface surface 624. They may be arranged in a pattern such as a grid layout or a radial layout.

Figure 34:
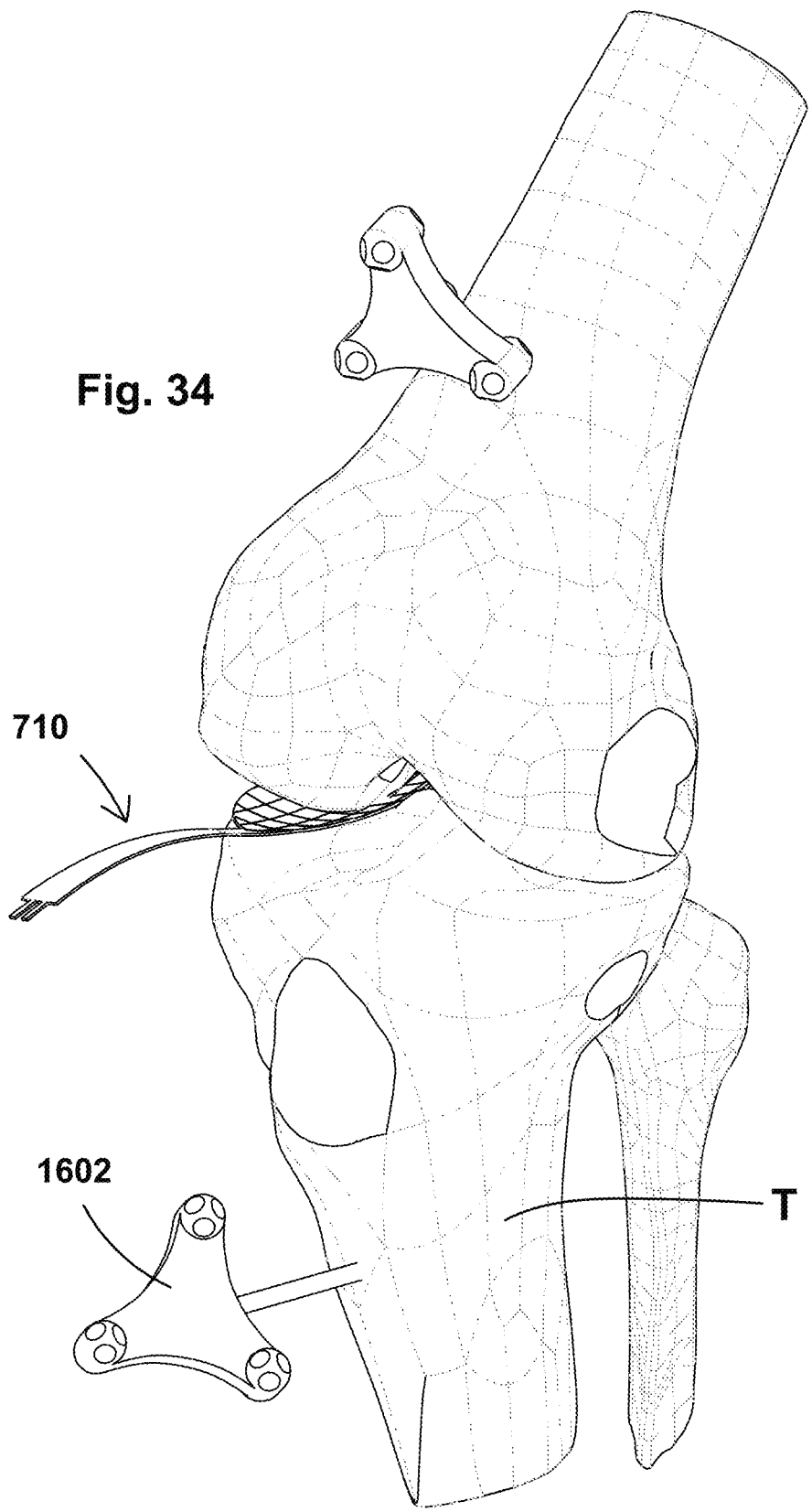
FIG. 34 is a schematic view of another exemplary embodiment of a gap balancer for a human knee joint.
Figure 35:
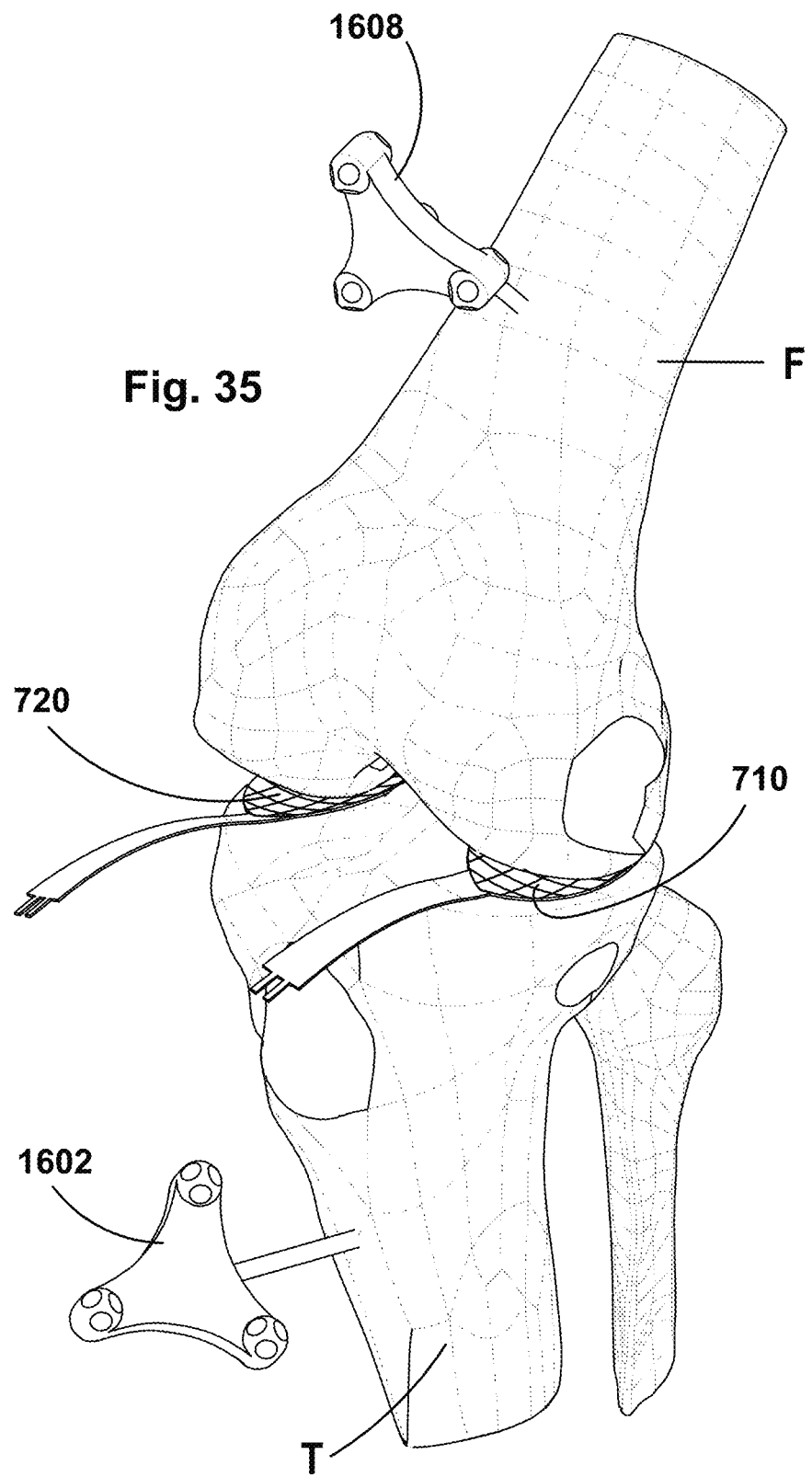
FIG. 35 is a schematic view of another exemplary embodiment of a gap balancer for a human knee joint.

FIGS. 34 and 35 illustrate another embodiment of a gap balancer 710. This device is substantially the same in structure and function to gap balancer 610, with the primary difference being that it is not U-shaped in plan view. Rather, it is shaped and sized to fit a single condyle of the knee joint. As shown in FIG. 34, a single gap balancer 710 may be used in a single condyle procedure. Alternatively, a balancing procedure could be carried out using two single-lobe devices 710 approaching from the medial and lateral aspects, respectively. This approach is shown in FIG. 35.

Figure 36:
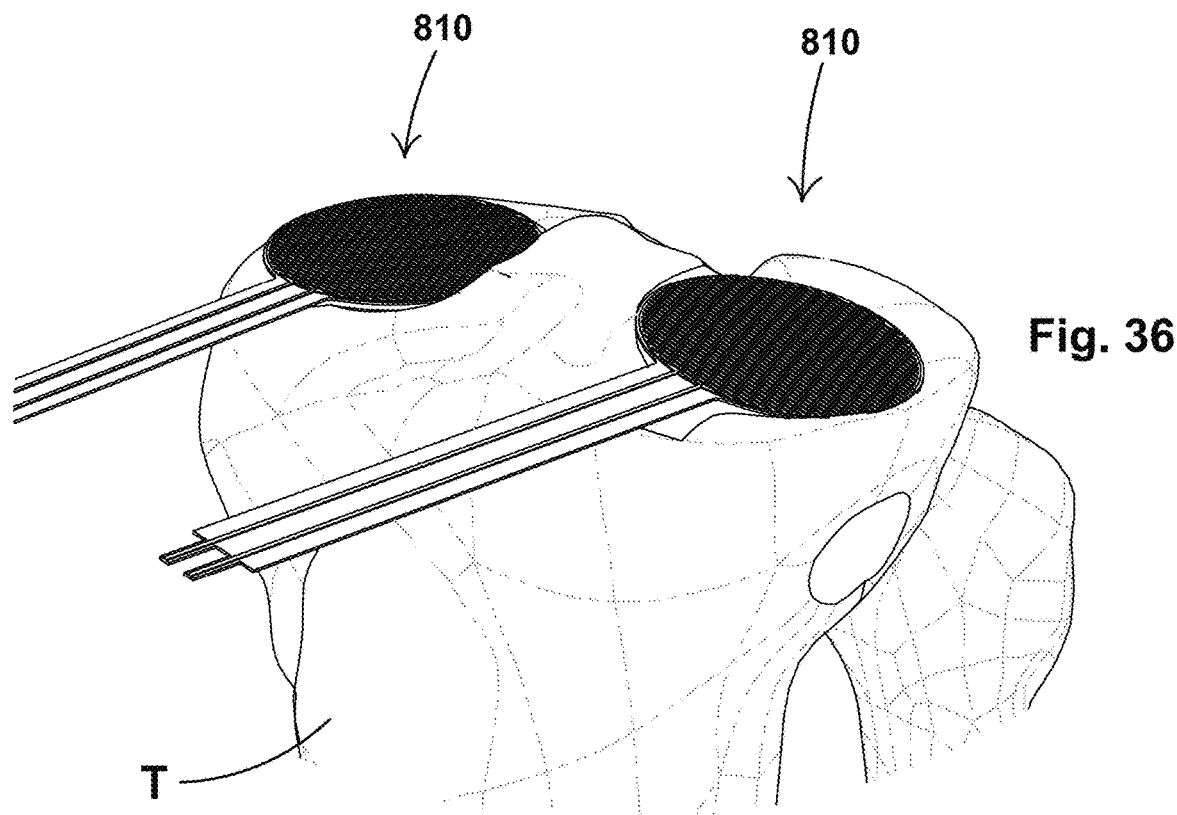
FIGS. 36 and 37 are schematic views of another exemplary embodiment of a gap balancer for a human knee joint.
Figure 37:
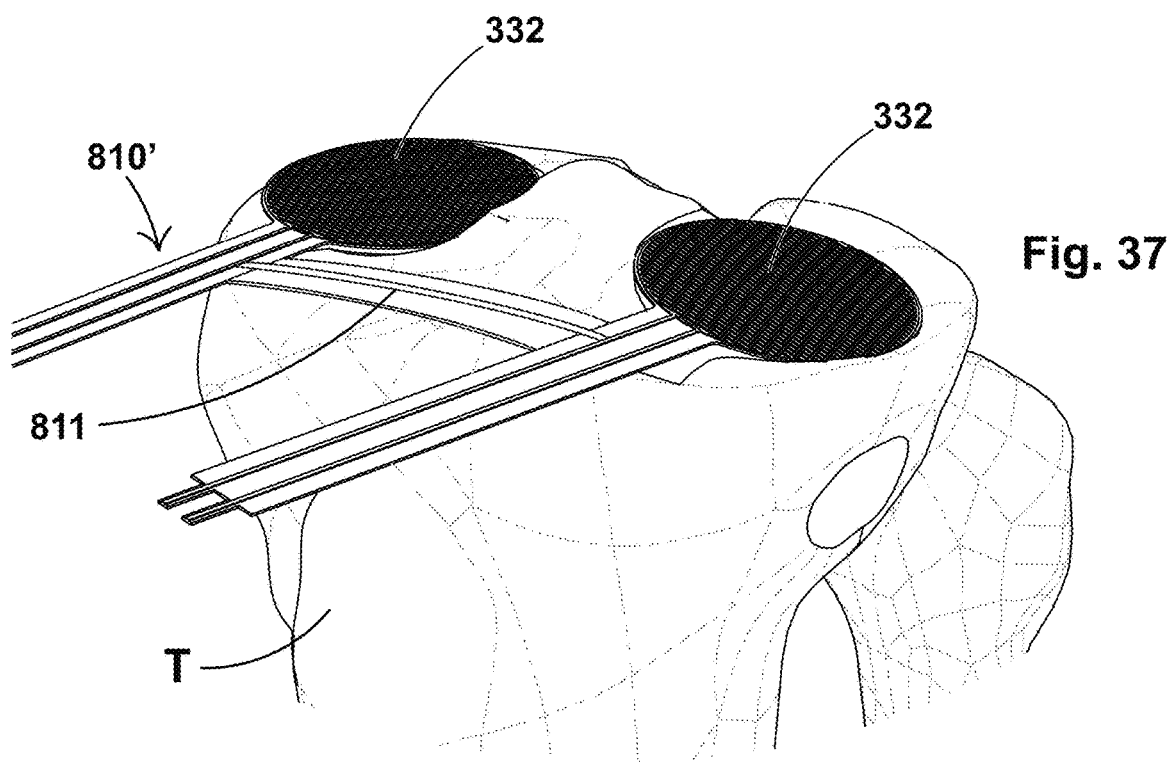
Figure 38:
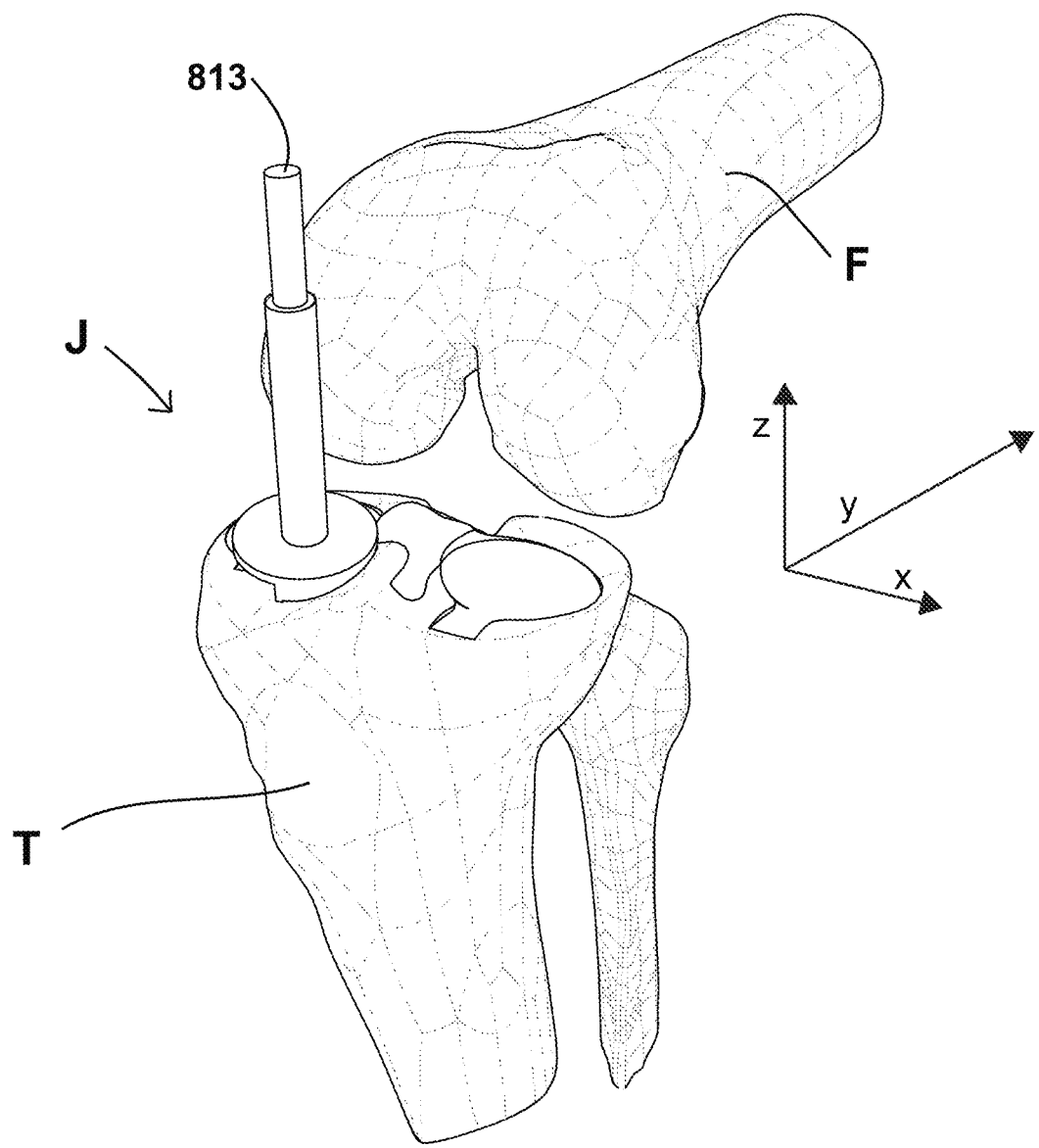
FIG. 38 is a perspective view of a knee joint being prepared for a gap balancer.

FIG. 36 illustrates another embodiment of a gap balancer 810. This device is similar in structure and function to gap balancer 710 and may include tibial and/or femoral sensors as described above. In FIG. 36, two individual gap balancers 810 are provided, one for each condyle. In FIG. 37, two gap balancers 810 are connected by a bridging element 811, to constitute a gap balancer 810'. The gap balancer 810 or 810' is used by being placed in a counterbore formed in a tibia T, using an appropriate cutting tool such as the drill bit 813 shown in FIG. 38.

Figure 39:
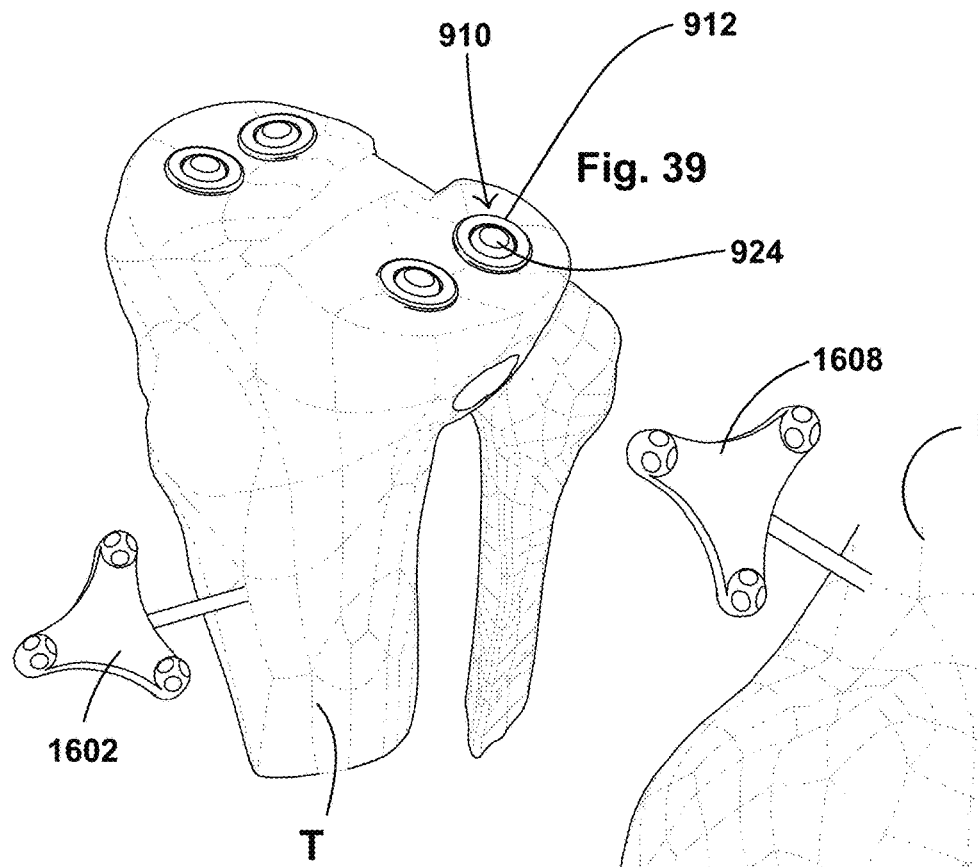
FIGS. 39 and 40 are schematic views of another exemplary embodiment of a gap balancer for a human knee joint.
Figure 40:
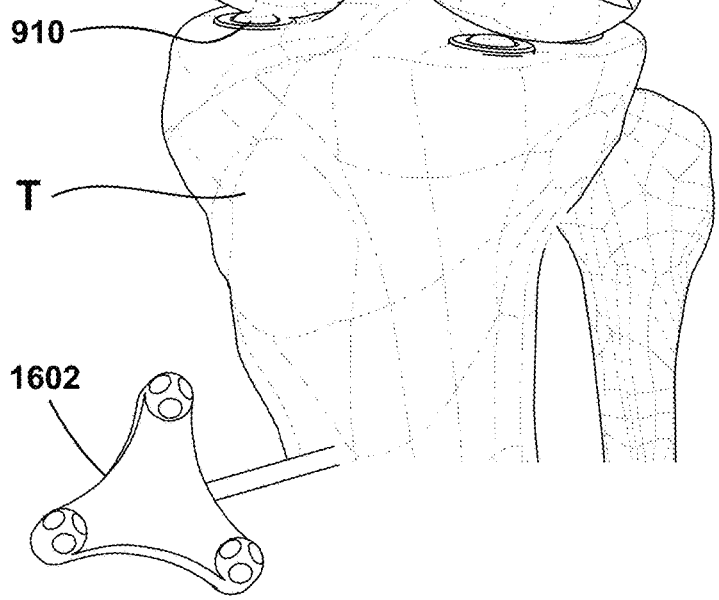

FIGS. 39 and 40 illustrate another embodiment of a gap balancer 910. It comprises a body 912 with a femoral interface surface 924 and an opposed tibial interface surface 920 (hidden in this view). The gap balancer 910 is generally shaped like a disk or puck. It is configured to move between a retracted position and an extended position, for example by being made in two or more pieces or by being extendable in response to the introduction of fluid pressure in its interior. In the illustrated example, the gap balancer 910 is provided with a single tibial force sensor and a single femoral force sensor similar to the sensors described above.

Figure 41:
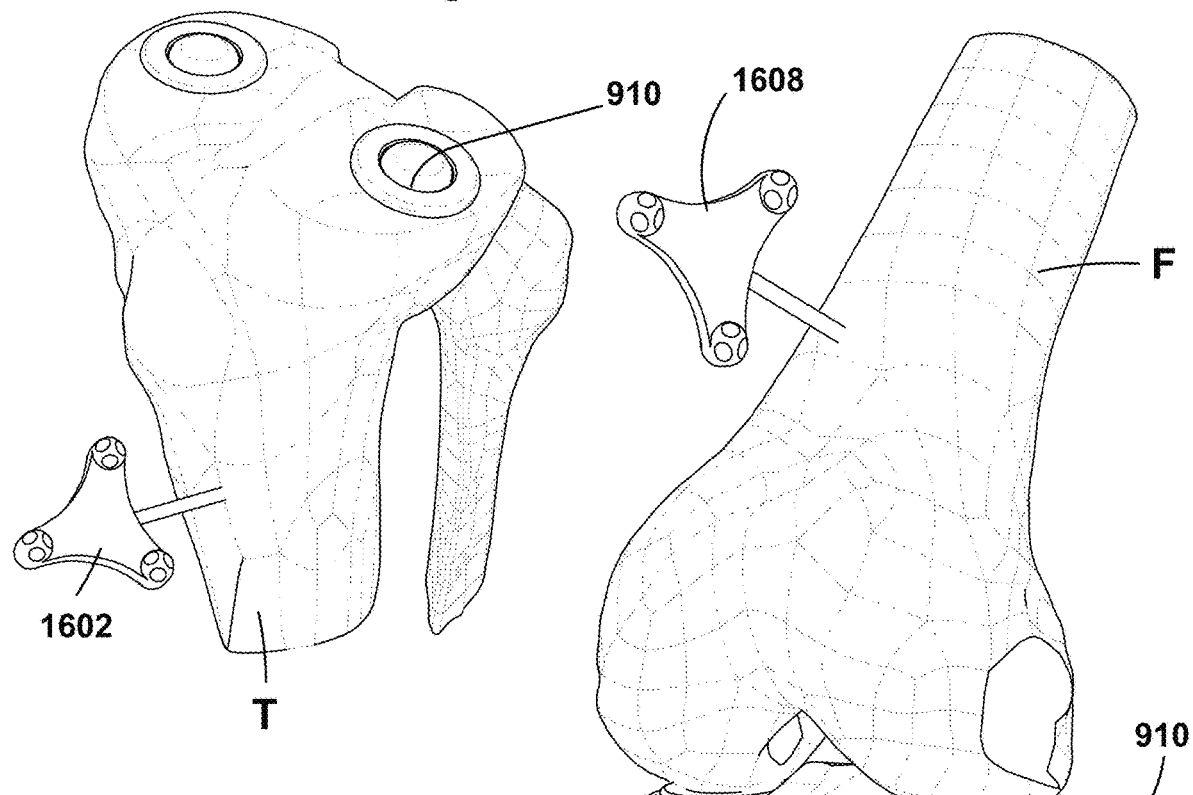
FIGS. 41 and 42 are schematic views of another exemplary embodiment of a gap balancer for a human knee joint.
Figure 42:
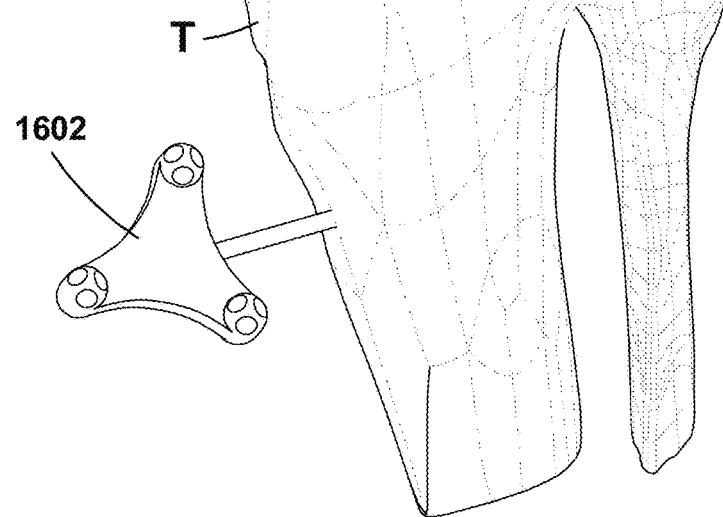

Two or more of the gap balancers 910 may be employed by implanting them into small recesses or counterbores in the tibia, in measured locations. Each gap balancer 910 thus provides a single-point reference of force, pressure, and/or deflection. In the example shown in FIG. 39 and FIG. 40, four of the gap balancers 910 are used, one positioned at the anterior and posterior aspect of each condyle. In the example shown in FIG. 41 and FIG. 42, two of the gap balancers 910 are used, one for each condyle.

Figure 43:
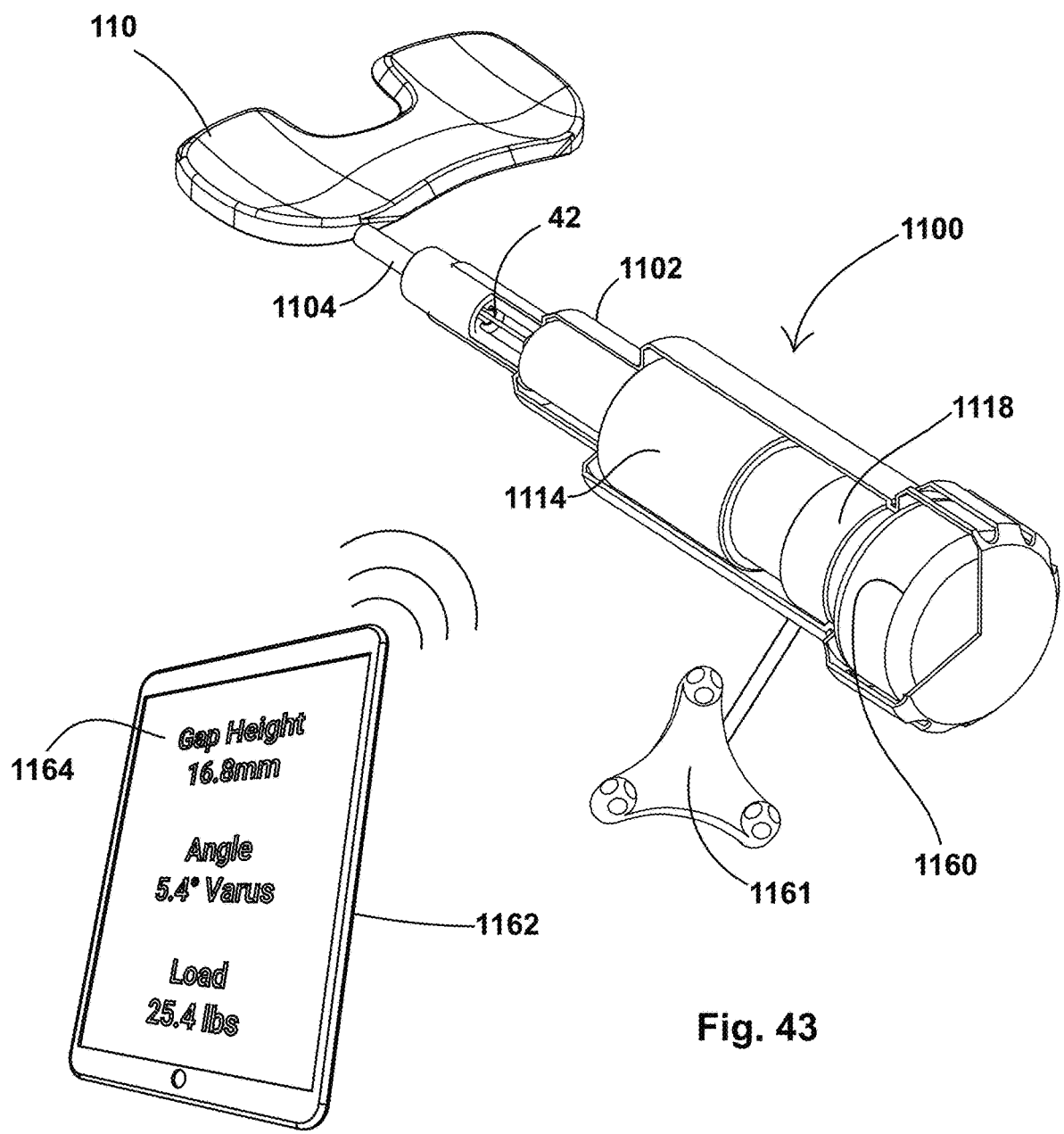
FIG. 43 is a perspective view of a gap balancer coupled to an exemplary actuating instrument.

FIG. 43 illustrates an exemplary actuating instrument 1100 for use with the gap balancer 10 or similar embodiments described above. The actuating instrument 1100 includes a barrel 1102 with an instrument coupler 1104 at its distal end. The proximate end of the barrel 1102 is connected to an actuating assembly 1118. The interior of the actuating assembly 1118 includes an appropriate driving mechanism such as an electrically-powered linear actuator 1114. The driving mechanism 1114 is operable to apply an actuating load to the gap balancer 10, through cable 42. Alternatively, distraction of the gap balancer 10 could be powered by electric power or pressurized fluid provided by the actuating assembly 1118. The actuating instrument 1100 includes an electronic data transmitter, shown schematically at 1160, and may include an appropriate electrical power source such as a battery (not shown). The transmitter 1160 may operate over a wired or wireless connection.

The actuating instrument 1100 and/or the gap balancer 10 may be supplied with an appropriate combination of transducers (not shown) to detect physical properties such as force and/or applied load and generate a signal representative thereof. For example, the balancer 10 may be provided with sensors operable to detect the magnitude of extension (i.e., "gap height") and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers. The transmitter 1160 is operable to transmit the sensor signal. A remote display 1162 is configured to receive the signal and produce a display 1164 of the transducer data. As one example, the remote display 1162 may be embodied in a conventional portable electronic device such as a "smart phone" or electronic tablet with suitable software programming.

In use, the remote display 1162 permits the surgeon to observe the physical properties of the gap balancer 10 in real time as the actuating instrument 1100 is used to operate the gap balancer 10. Optionally, the actuating instrument 1100 may incorporate a tracking marker 1161. It includes one or more tracking points (not individually illustrated) which may be configured as transmitting antennas, radiological markers, or other similar devices. Using an appropriate receiving device, such as the remote display described in more detail below, the position and orientation of the receiving device to the tracking marker 1161 may be determined by receipt and analysis at the receiving device of signals transmitted by the tracking marker 1161.

Figure 44:
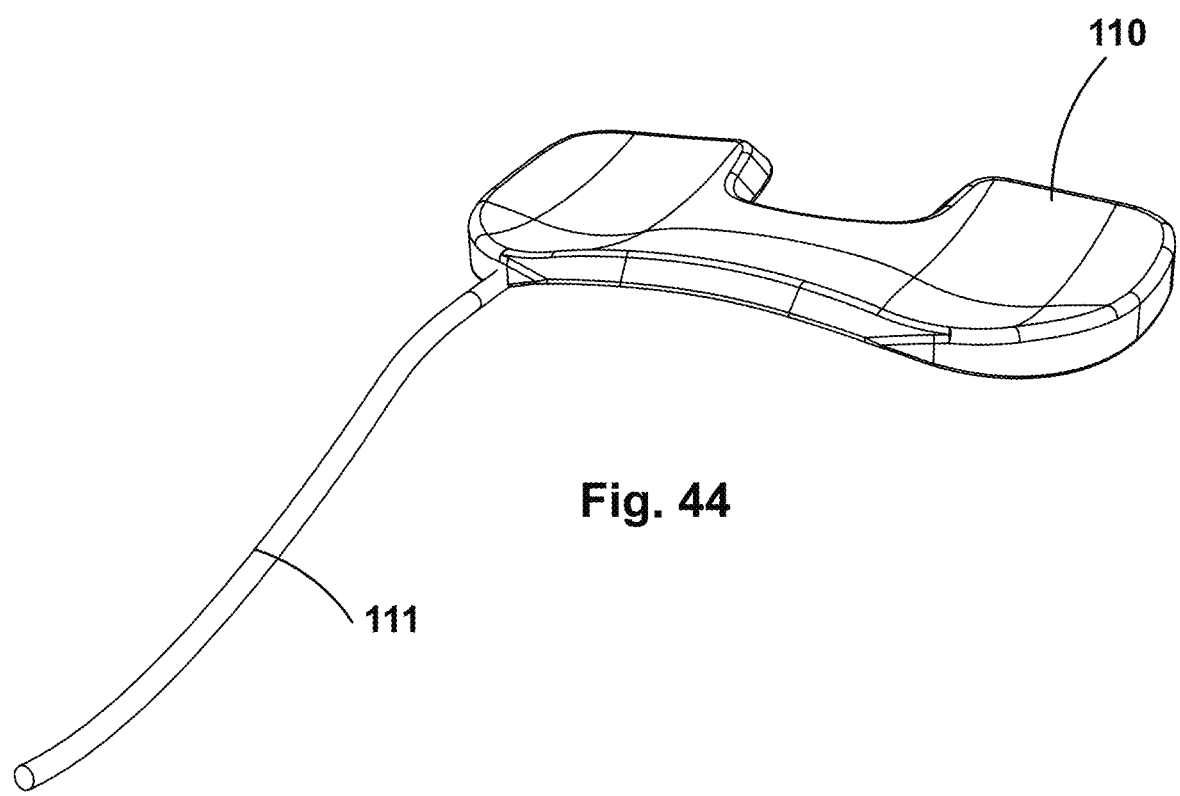
FIG. 44 is a schematic view of a gap balancer having a flexible connection.
Figure 45:
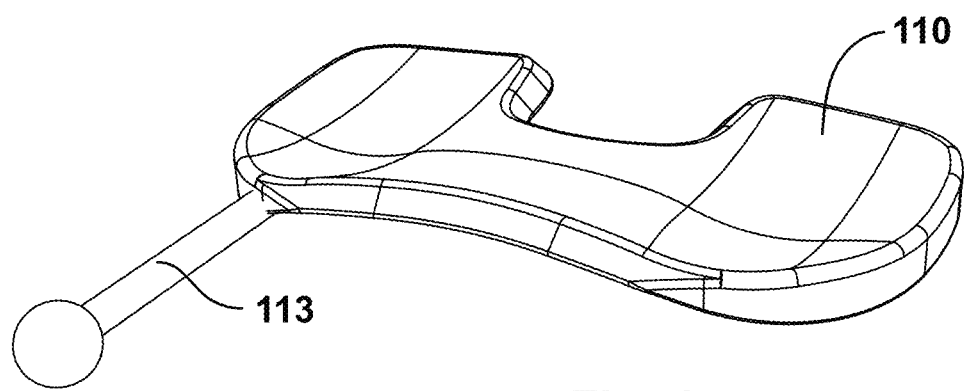
FIG. 45 is a schematic view of a gap balancer having a wireless connection.

FIG. 43 illustrates a gap balancer 110 physically coupled to the actuating instrument 1100. FIG. 44 illustrates a gap balancer 110 having a flexible cable connection 111 for functions such as control, power, and/or data transmission. FIG. 45 illustrates a gap balancer having a transceiver 113 providing a wireless connection (e.g., transceiver and antenna) to an external device for functions such as control, power, and/or data transmission.

FIG. 46 in combination with FIG. 47 illustrates a gap balancer having a wireless data connection to an external display device as described elsewhere herein. In FIG. 47, information such as gap height, coronal plane angle, and load are displayed in text. The visualization of loading can also be represented graphically, as shown by the example graphics in FIG. 48.

FIGS. 49-54 illustrate a gap balancer 110 inserted into a knee joint J and being used to distract the joint and/or collect data, in combination with various configurations of tracking markers as described elsewhere herein.

Figure 49:
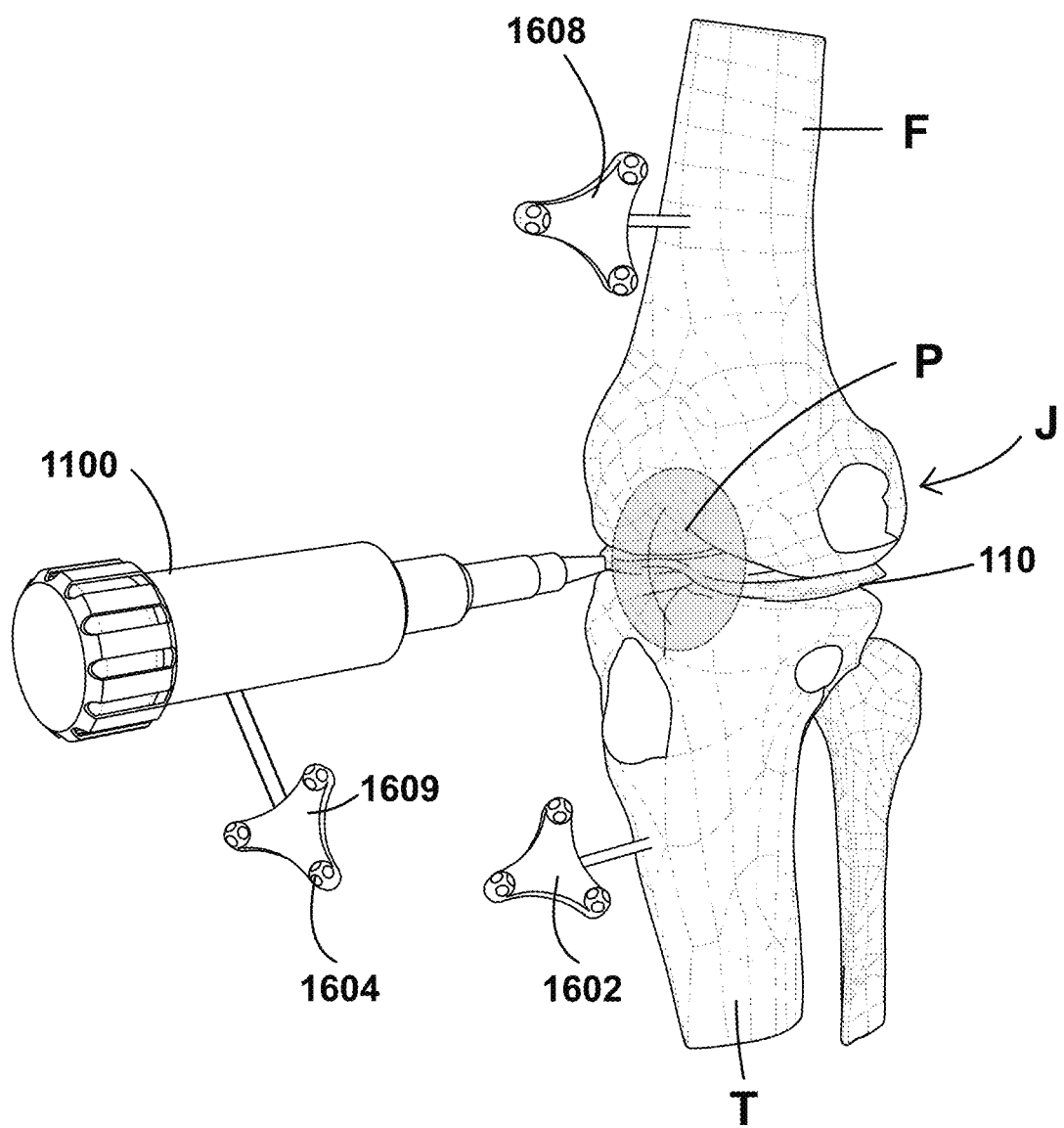
FIG. 49 is a view of a human knee joint in extension with a gap balancer inserted therein and tracking markers coupled thereto.
Figure 50:
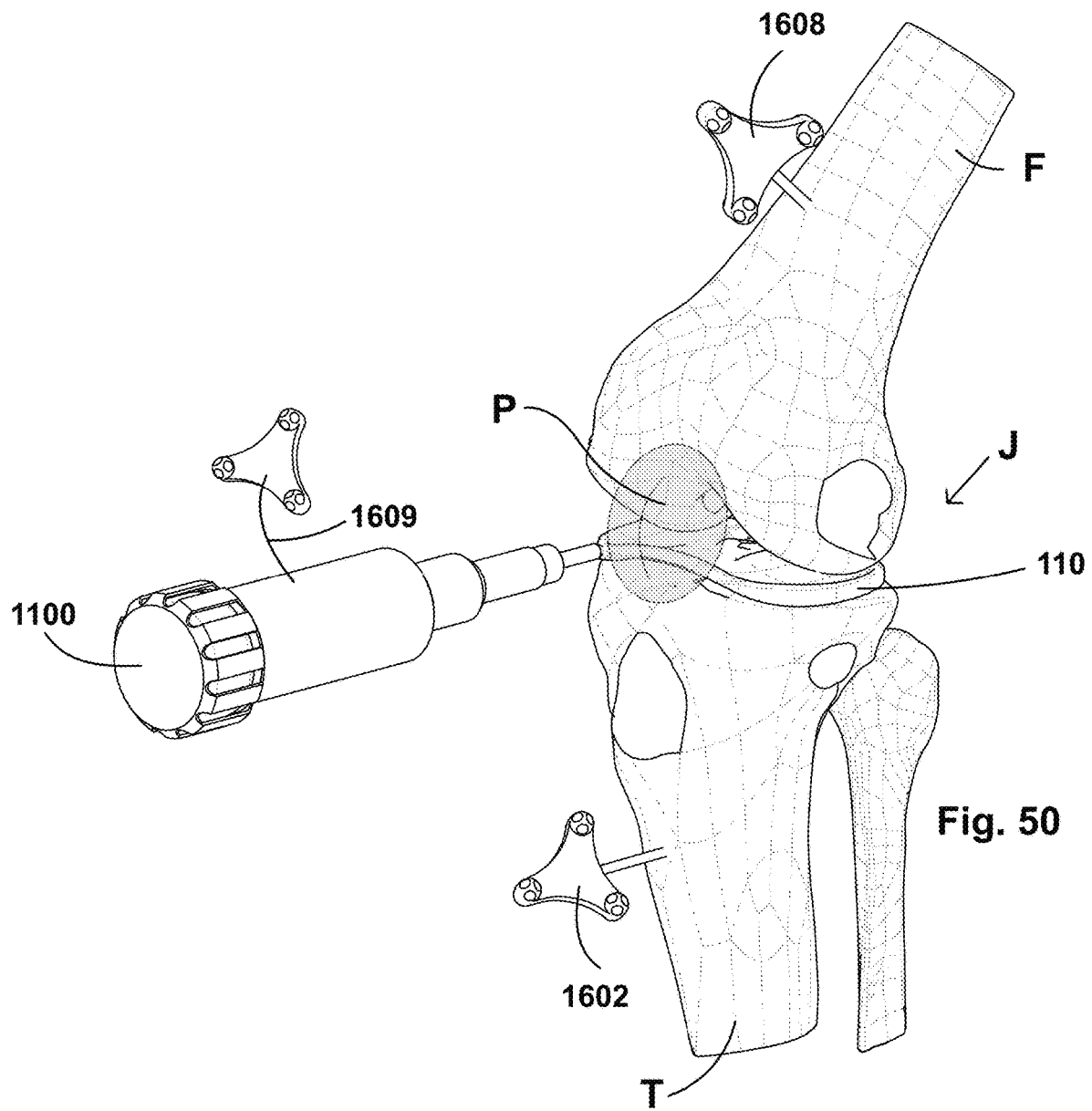
FIG. 50 is a view of the knee joint of FIG. 49 in a mid-flexion position.
Figure 51:
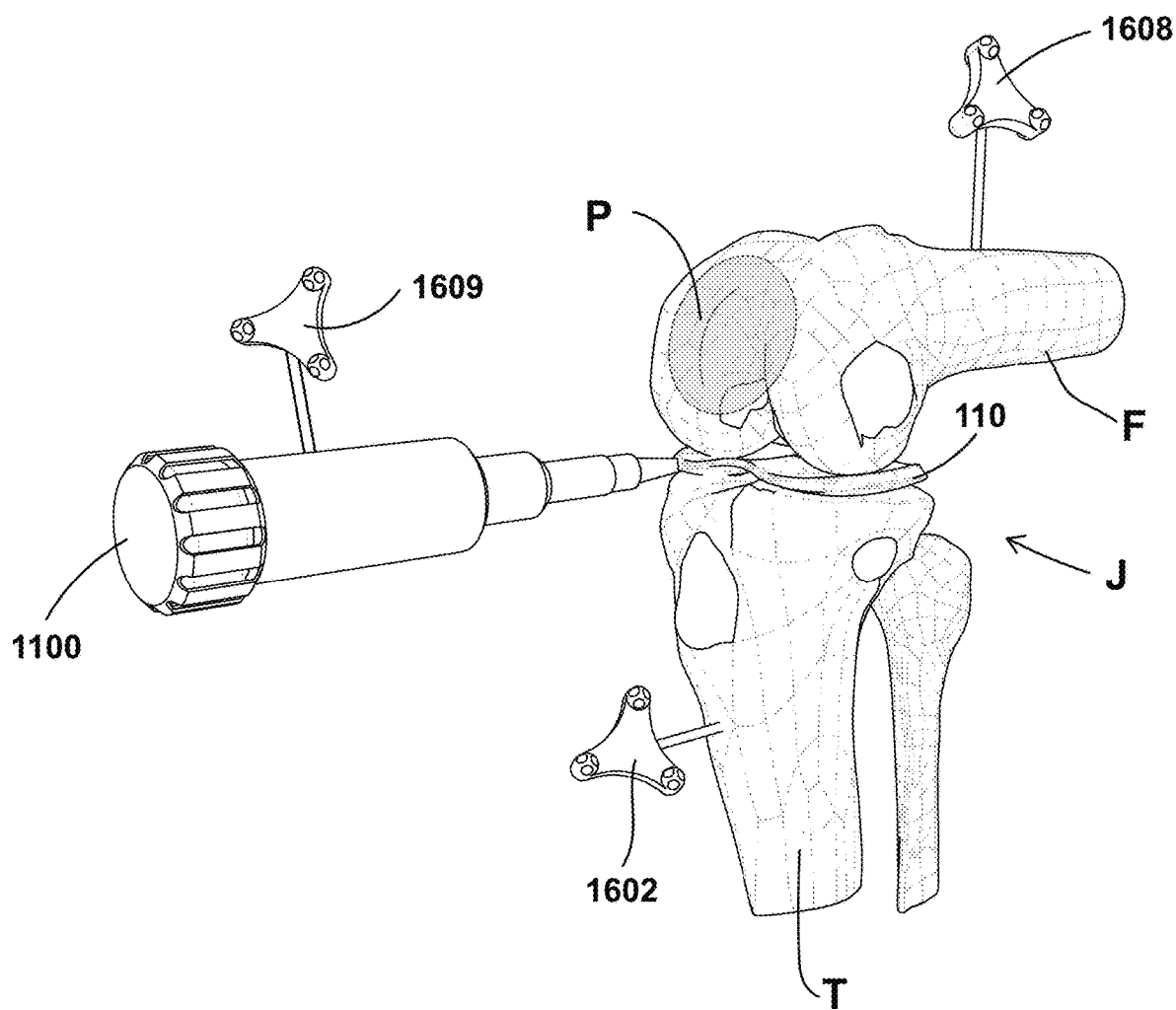
FIG. 51 is a view of the knee joint of FIG. 49 in a flexion position.

In FIG. 49, an actuating instrument 1100 is shown coupled to the gap balancer 110 inserted into the knee joint J between the tibia T and the femur F. A tracking marker 1602 is shown attached to the tibia T in such a way that it has a substantially fixed position and orientation relative to the tibia T. It includes one or more tracking points 1604 which may be configured as transmitting antennas, radiological markers, or other similar devices. Using an appropriate receiving device such as the illustrated instrument 1100 the position and orientation of the instrument 1100 relative to the tracking marker 1602 may be determined by receipt and analysis at the instrument 1100 of signals transmitted by the tracking marker 1602. Tracking marker 1602 and appropriate receivers are known within the state-of-the-art. Additionally, a second tracking marker 1608 is shown attached to the femur F in such a way that is has a substantially fixed position orientation relative to the femur F. Again, the position and orientation of the instrument 1100 relative to the tracking marker 1608 may be determined. Optionally, the instrument 1100 may be equipped with a separate tracking marker 1609.

Once the gap balancer 110, actuating instrument 1100, and tracking markers 1602 and 1608 are implanted, the joint J would then be moved to the range of full extension (FIG. 49) through mid-flexion (FIG. 50) to full flexion (FIG. 51), while monitoring the position of tracking markers 1602 and 1608. The path swept out by the tracking marker 1602 and 1608 is representative of the movement of one or more lobes of the condyle of the femur against the gap balancer 10.

The movement of tracking markers 1602 and 1608 relative to one another can be collected as data. These data could be stored, for example, as a set of paths, coordinates, curves, or maps representing the condyle, referenced to the tracking marker 1608. These data can then also be translated to determine the position of the condyle of the femur F against the gap balancer. This position data is useful because it defines the outer shape or profile or geometry of the articular surface of the native, pre-cut femoral condyle against the instrument 1100. This defined articular surface profile can then be compared to an ideal articular surface profile that can be created by removing native bone and subsequently implanting a prosthetic condyle. It is noted that the movement of the knee joint J through its range of movement is not a pure pivoting or rotational movement, but includes a combination of rotation and translation. The path the knee joint J follows is responsive to the effect of multiple forces and interacting structures. The data from tracking markers described above is useful for accurately describing the geometry of the joint J to incorporate these multiple effects.

Figure 52:
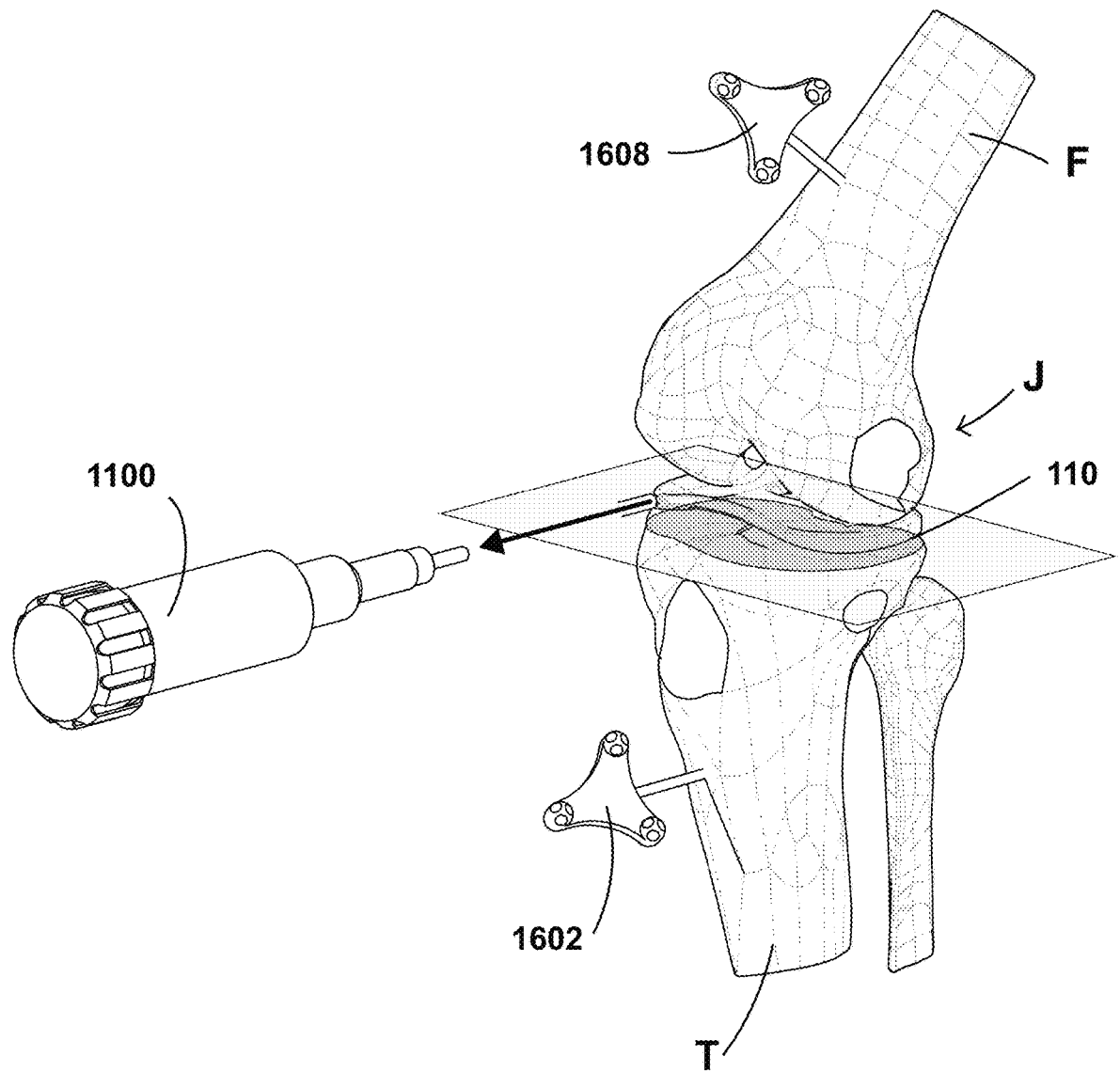
FIG. 52 is a view of a human knee joint having a gap balancer inserted therein and tracking markers coupled thereto, in wireless communication with an actuating instrument.

FIG. 52 shows a gap balancer 110 inserted into a knee joint J which is provided with tracking markers 1602 and 1608. In this example, the gap balancer 10 has a wireless data connection to an actuating instrument 1100.

Figure 53:
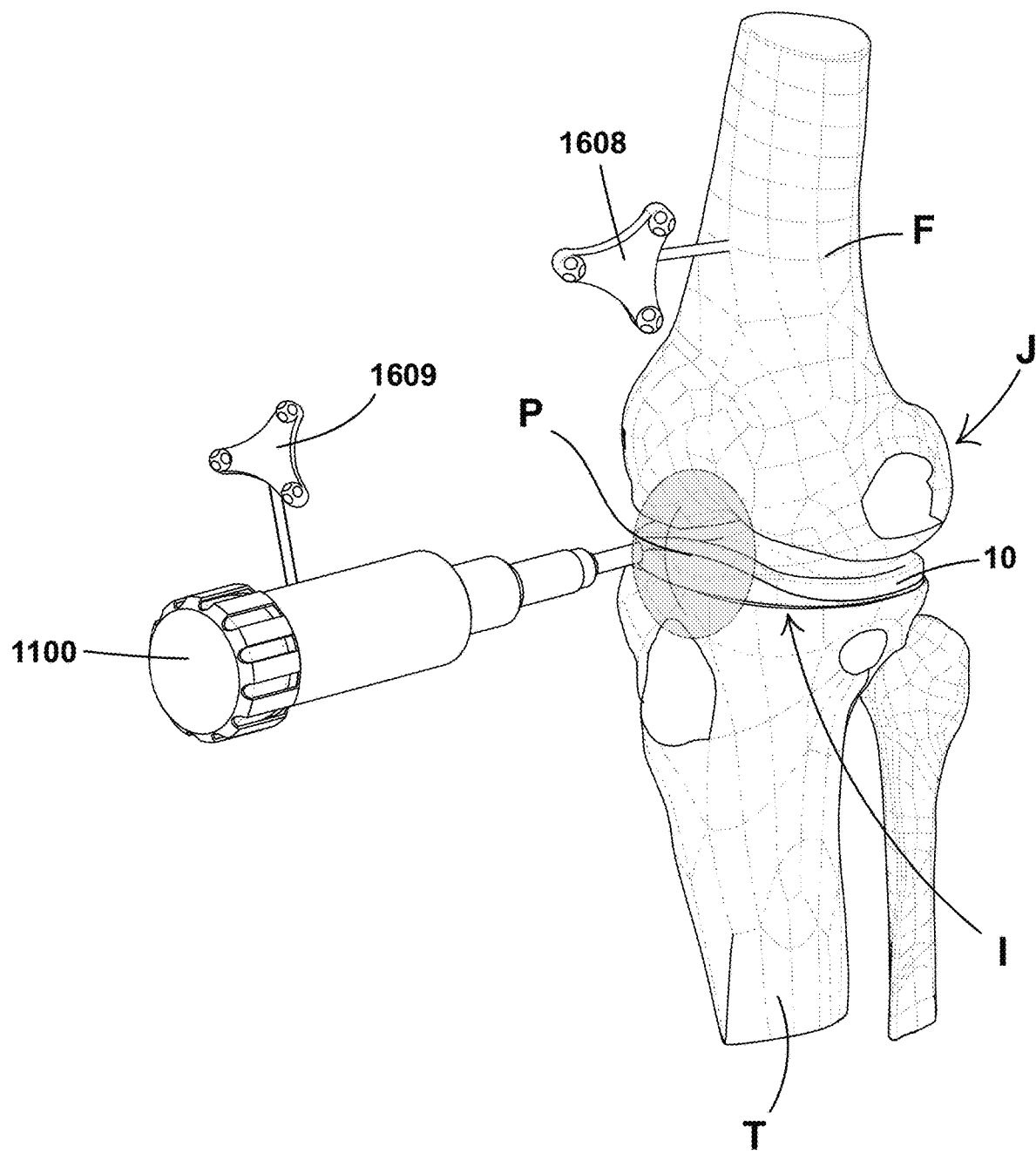
FIG. 53 is a view of the human knee joint having a gap balancer inserted therein and coupled to an actuating instrument.

FIG. 53 shows a gap balancer 10 of the type illustrated in FIG. 6 inserted into knee joint J which is provided with tracking marker 1608. In this example, proximal tibia resection (tibial plateau cut) has already been carried out. The tibial cut plane 1 exists in a known location relative to the entire system (including the gap balancer 10 and femoral tracker 1608). So, no tibia tracker is necessary.

Figure 54:
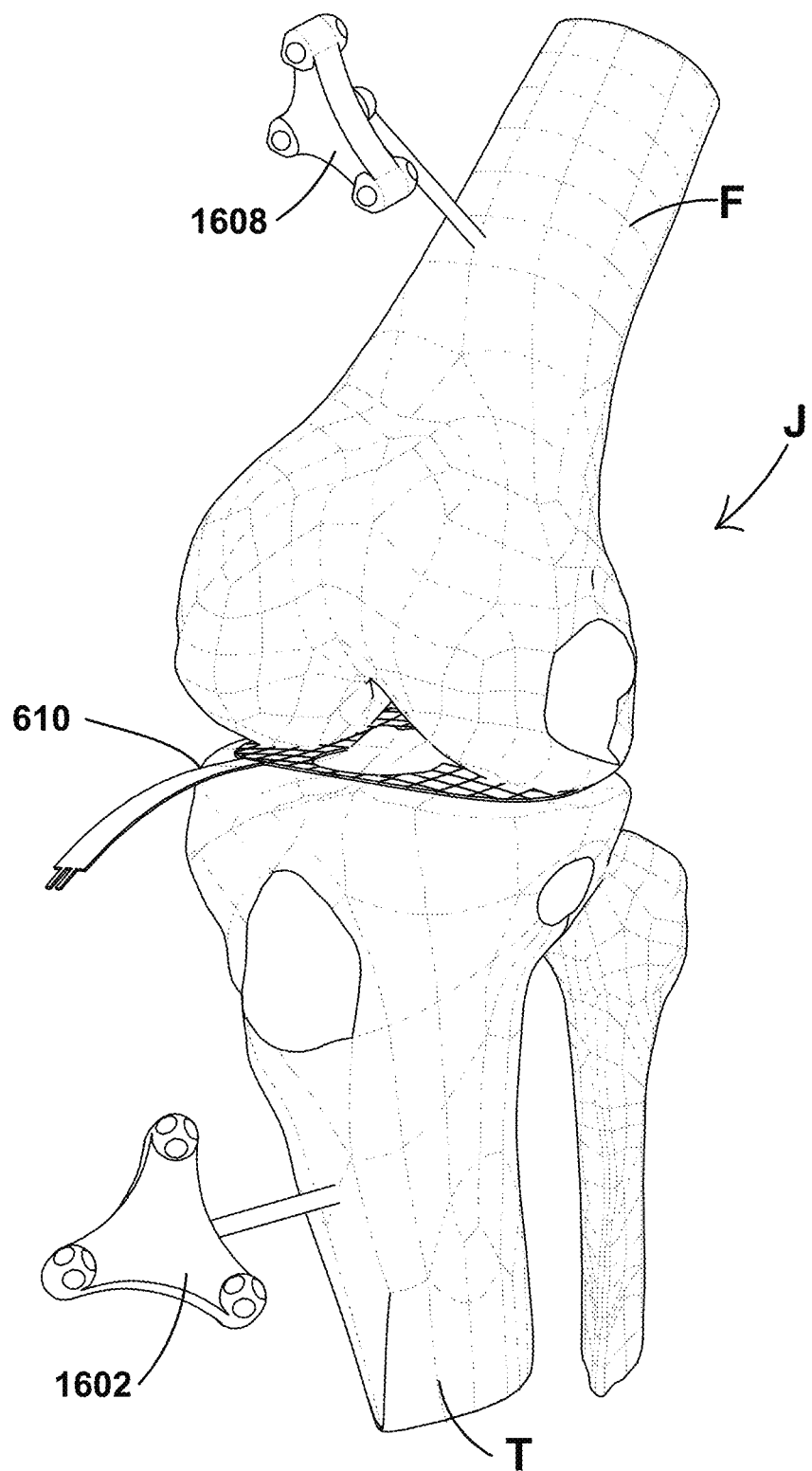
FIG. 54 is a view of a human knee joint in extension with a gap balancer inserted therein and tracking markers coupled thereto.

FIG. 54 shows a gap balancer 610 of the type illustrated in FIG. 31 inserted into knee joint J which is provided with tracking markers 1608 and 1602. No proximal tibia resection is present.

The gap balancer of the embodiments shown in FIGS. 6-42 may be used, as an example, to collect force or pressure data which can then be used to characterize the knee joint in various ways. This method is further described with reference to FIGS. 55-66.

Figure 55:
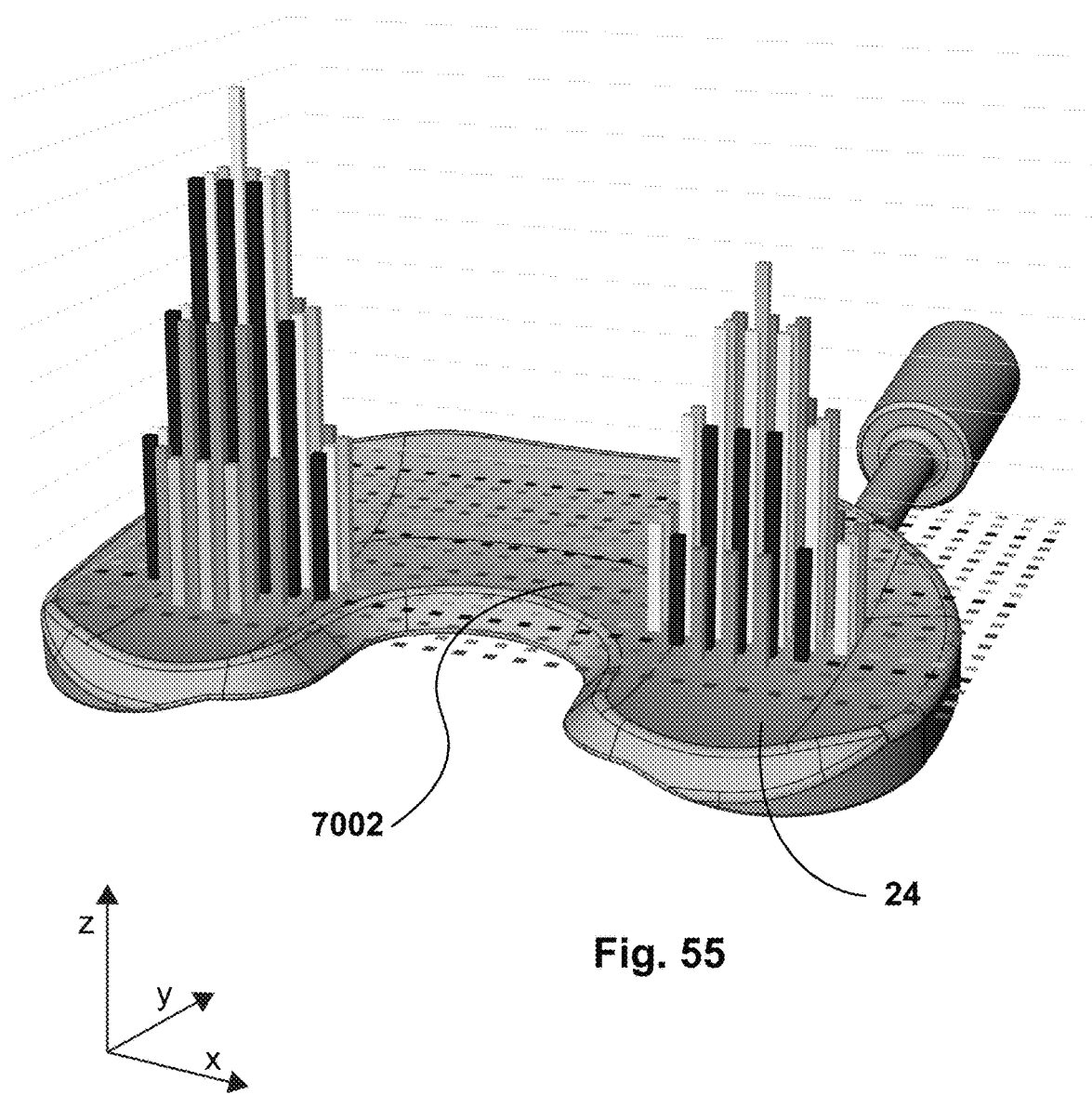
FIG. 55 is a schematic perspective view of a gap balancer having a sensor array, with example sensor data superimposed thereon.

FIG. 55 shows a 3D bar graph of force magnitude (Z-direction height) produced by the femoral condyle (not shown) for each sensor element 7002 superimposed on the image of the femoral interface surface 24. The illustrated image shows two primary contact zones representing the contact of each femoral condyle on the surface of the device or the contact force between the femoral condyles and the corresponding tibial plateaus (the graphs would look very similar). It can be seen that this data can be used to map the geometry and/or position of the femoral condyle. This mapping may be carried out, for example by inserting the gap balancer 10 between the femur F and the tibia T, and moving the knee joint J through some or all of its range of motion while recording data from the sensor elements 7002 using the electronic receiving device to collect the force data and (optionally) to collect position data from at least one tracking marker. If tracking marker data is also collected, the force data would be correlated to the position data. In other words, the tracking marker data may be used to confirm the joint extension/flexion position at which force data is being collected.

Figure 56:
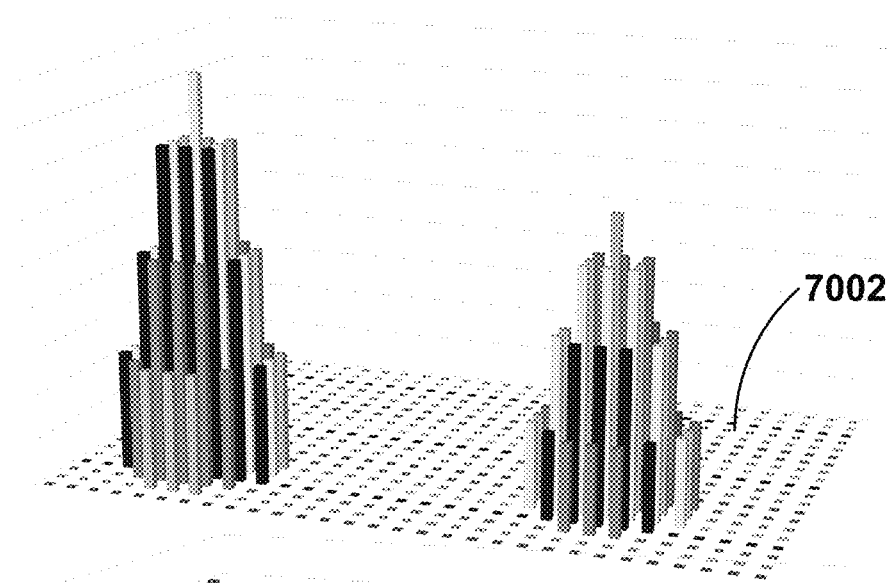
FIG. 56 is a graph showing representative data produced by sensor of a gap balancer, with a knee joint in the fully extended position.
Figure 57:
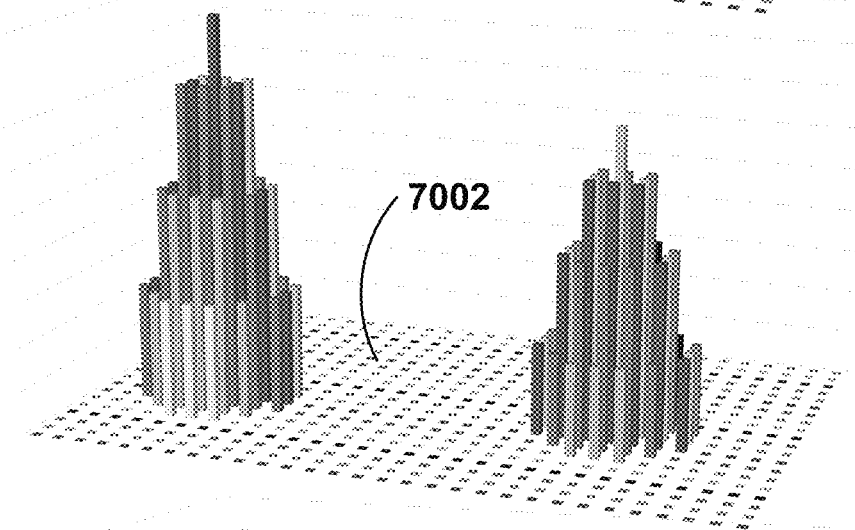
FIG. 57 is a graph showing representative data produced by sensor of a gap balancer, with the knee joint in a mid-flexion position.
Figure 58:
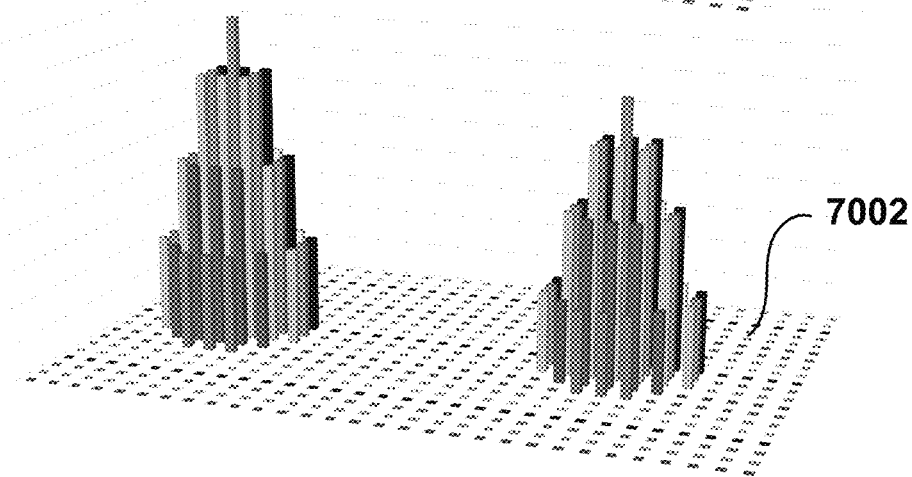
FIG. 58 is a graph showing representative data produced by sensors of a gap balancer with the knee joint in a 90-degree flexed position.

FIG. 56 shows representative force data produced by the two condyles with the knee joint J in a fully extended position. FIG. 57 shows representative force data produced by the two condyles of the knee joint J in a mid-flexion position, for example flexed approximately 45° away from the fully extended position. Finally, FIG. 58 shows representative force plots produced by the two condyles with the knee joint J in a 90-degree flexed position.

Figure 59:
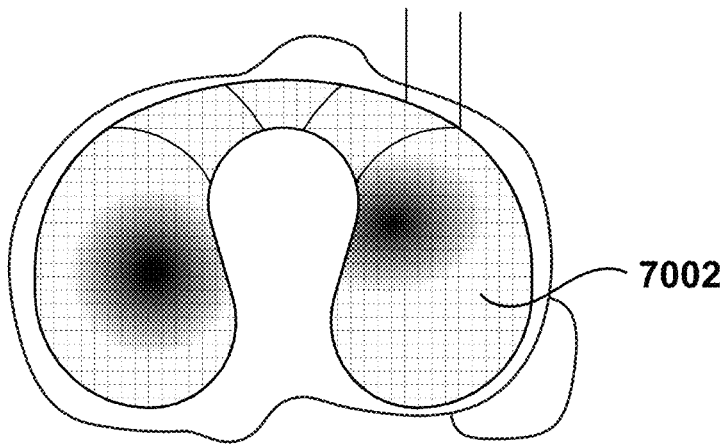
FIG. 59 is a plot showing instantaneous medial and lateral contact patches of the human knee joint, with the knee in the fully extended position.
Figure 60:
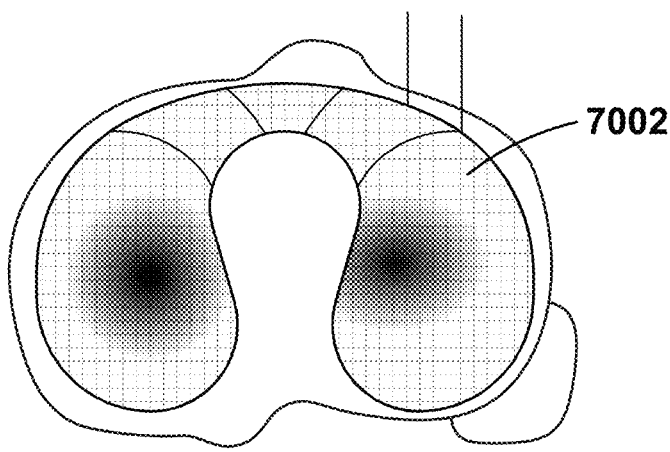
FIG. 60 is a plot showing instantaneous medial and lateral contact patches of the human knee joint, with the knee in a mid-flexion position.
Figure 61:
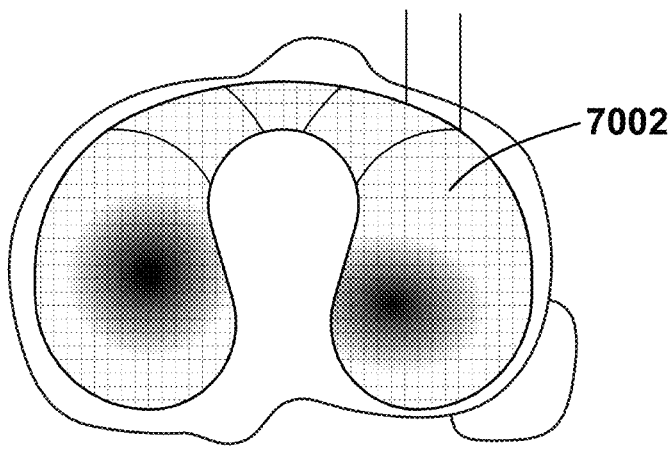
FIG. 61 is a plot showing instantaneous medial and lateral contact patches of the human knee joint, with the knee in a 90-degree flexed position.

FIGS. 59-61 show examples of force data represented as a 2D surface plot. This is another means of illustrating the instantaneous medial and lateral contact patches between the femoral condyles in the tibial plateaus. In these views, darker areas indicate relatively higher force or pressure, and lighter colors indicate relatively lower force or pressure. The movement of the contact patches may be readily visualized as the knee joint J is moved from a fully extended position (FIG. 59) through a 45-degree mid-flexion position (FIG. 60) to a 90-degree flexion position (FIG. 61).

Figure 62:
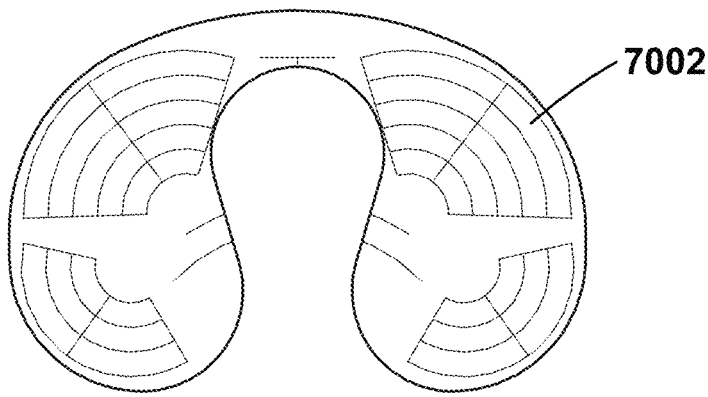
FIG. 62 is a schematic showing an example of sensors arrayed as arcuate segments.
Figure 63:
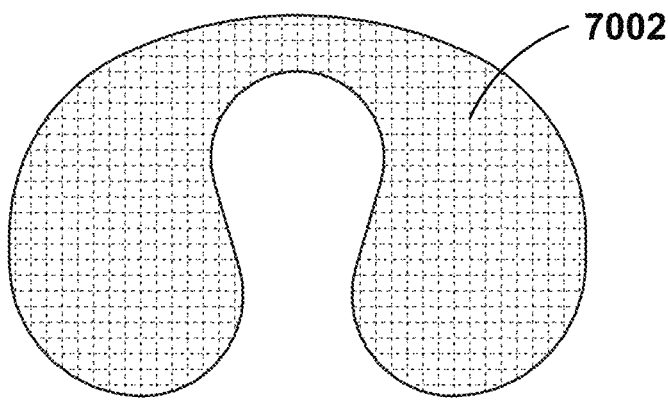
FIG. 63 is a schematic showing sensors arrayed in a 2D grid pattern.
Figure 64:
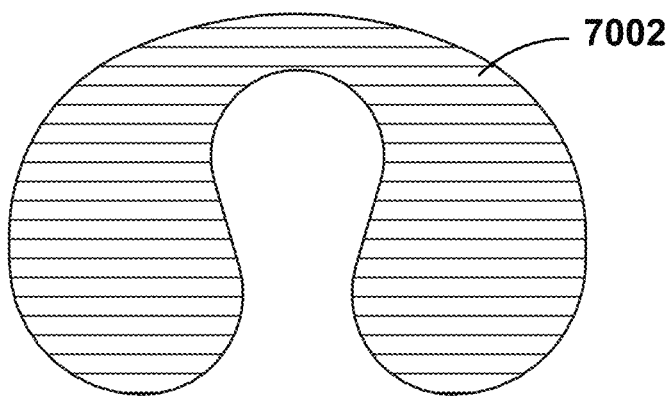
FIG. 64 is a schematic showing sensors arrayed as a series of parallel strips or bands.

In FIGS. 59-61, the sensor array is shown configured in an orthogonal X-Y grid pattern. The sensor pattern may be configured to suit a particular application. FIG. 62 shows an example of sensors arrayed as arcuate segments. FIG. 63 shows sensors arrayed in a 2D grid pattern, and FIG. 64 shows sensors arrayed as a series of parallel strips or bands.

Figure 65:
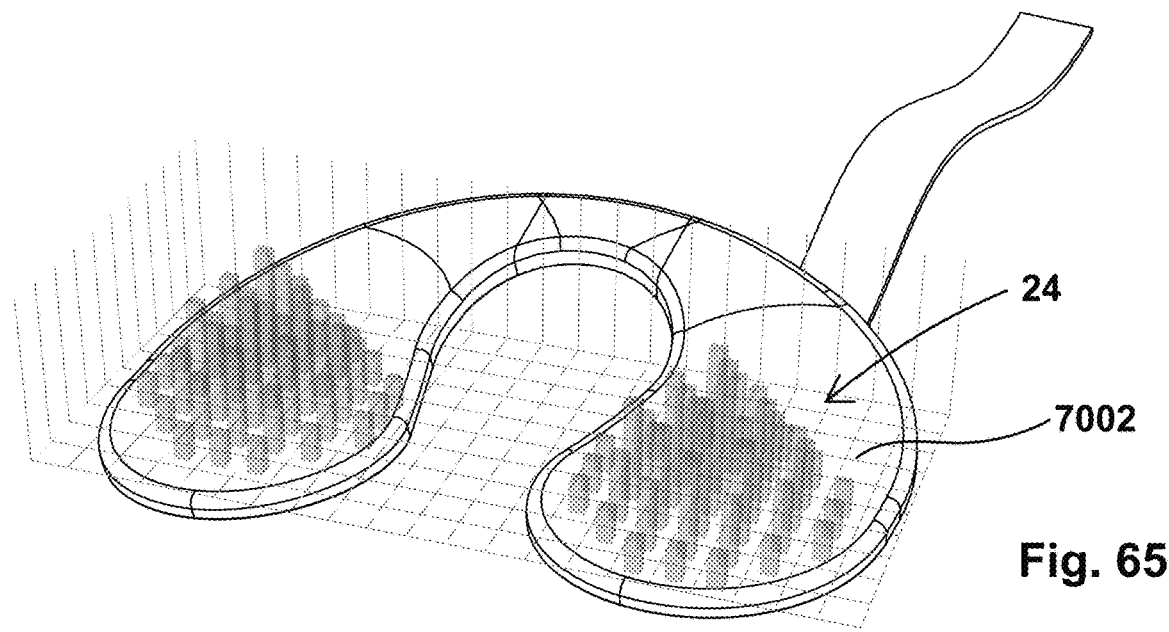
FIG. 65 is a schematic perspective view of a gap balancer having a sensor array, with example sensor data superimposed thereon.
Figure 66:
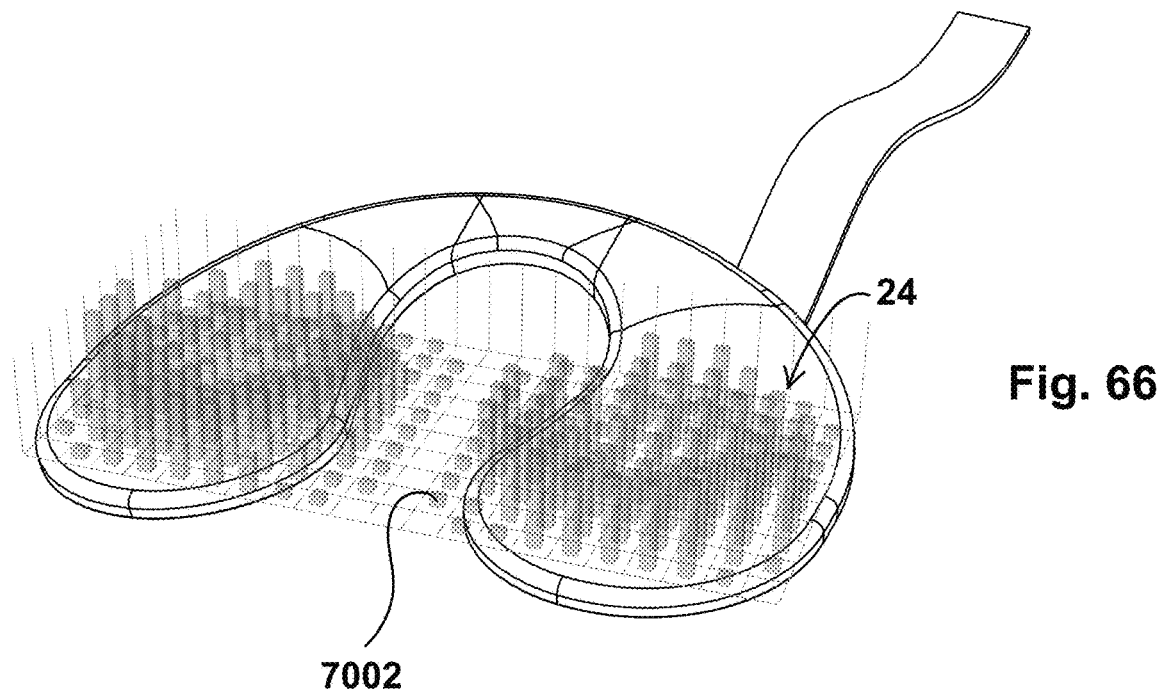
FIG. 66 is a schematic perspective view of a gap balancer having a sensor array, with example sensor data superimposed thereon.

FIG. 65 shows another exemplary 3D bar graph of force magnitude (Z-direction height) produced by the femoral condyle (not shown) for each sensor element 7002 superimposed on the image of the femoral interface surface 24. FIG. 66 is an exemplary 3D bar graph showing the corresponding local distraction or height for each sensor element 7002 superimposed on the image of the femoral interface surface 24.

Figure 67:
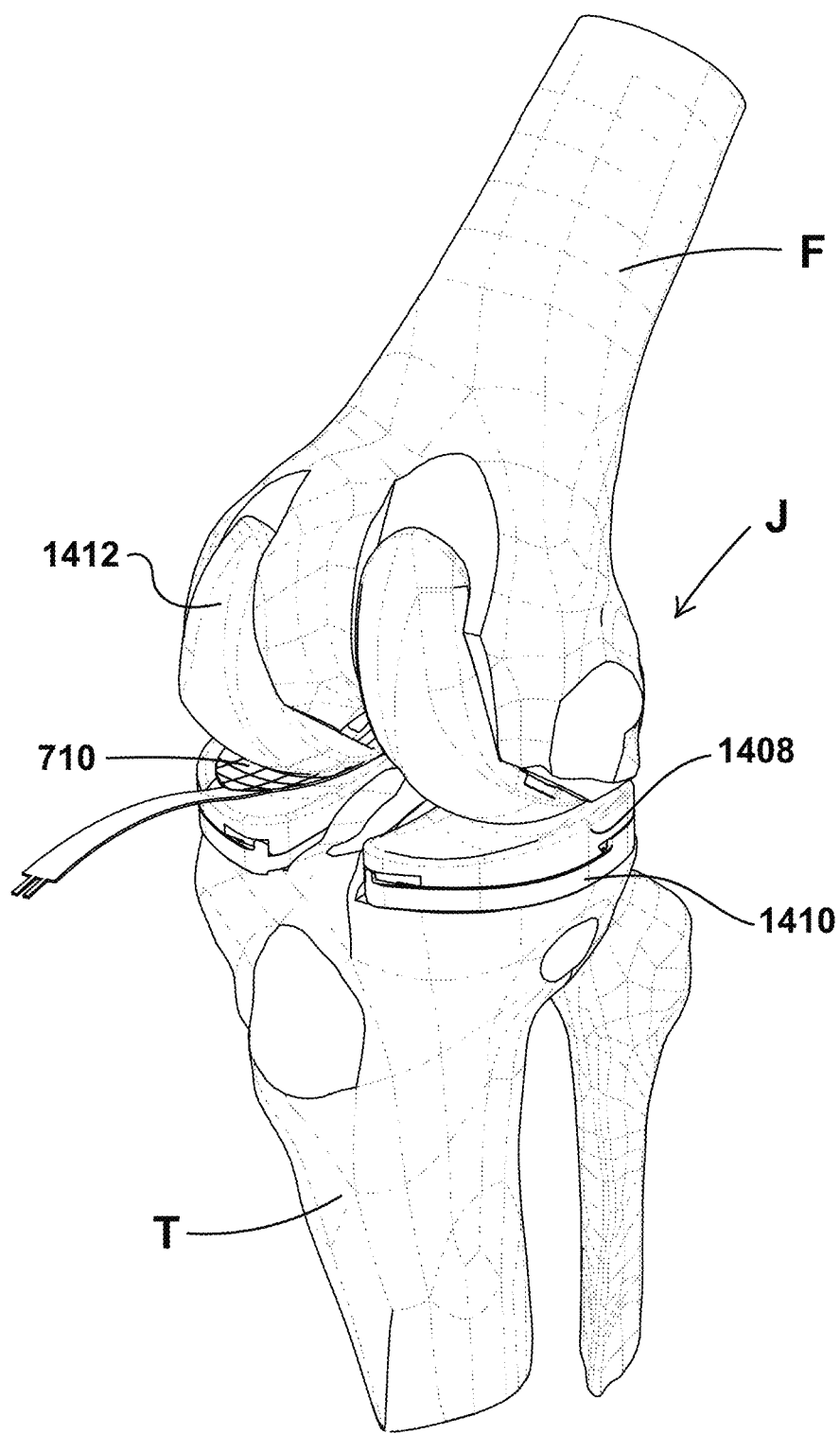
FIG. 67 is a schematic perspective view of a knee joint having an endoprosthesis implanted therein, with a gap balancer being inserted in one lateral compartment.

The gap balancer may be used to collect data before, during, or after a surgical procedure formed on the knee joint J. For example, FIG. 67 illustrates a knee joint J having an endoprosthesis 1408 of a known type implanted therein. The endoprosthesis 1408 includes a tibial component 1410 and a femoral component 1412. A gap balancer 710 of the embodiment shown in FIG. 34 is shown inserted between the tibial component 1410 and the femoral component 1412.

Figure 68:
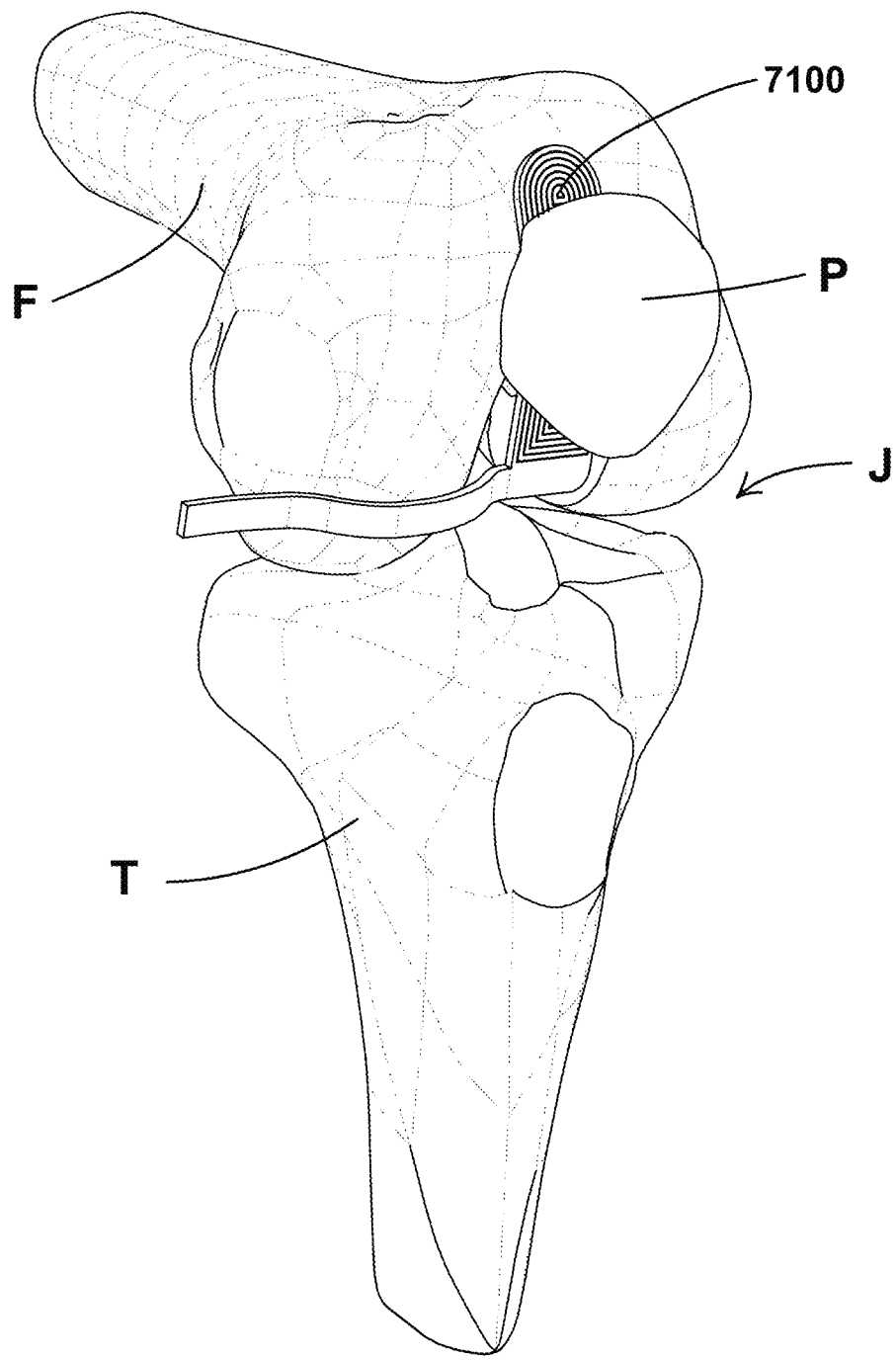
FIG. 68 is a schematic perspective view of a knee joint with a patella force sensor inserted between the femur and the patella.

In addition to collecting force, pressure, and/or displacement data between the femur F in the tibia T, an additional device may be used to collect force, pressure, and/or displacement data between the femur F and the patella P. FIG. 68 shows a human knee joint J in flexion. A patella force sensor 7100 is shown disposed between the patella P and the femur F. The patella force sensor 7100 may include one or more individual sensors operable to detect force, pressure, and/or displacement and produce representative signals, as described above with respect to the sensors of the gap balancer embodiments. This data may be transmitted through a flexible cable as shown in FIG. 68, or over a wireless connection.

Figure 69:
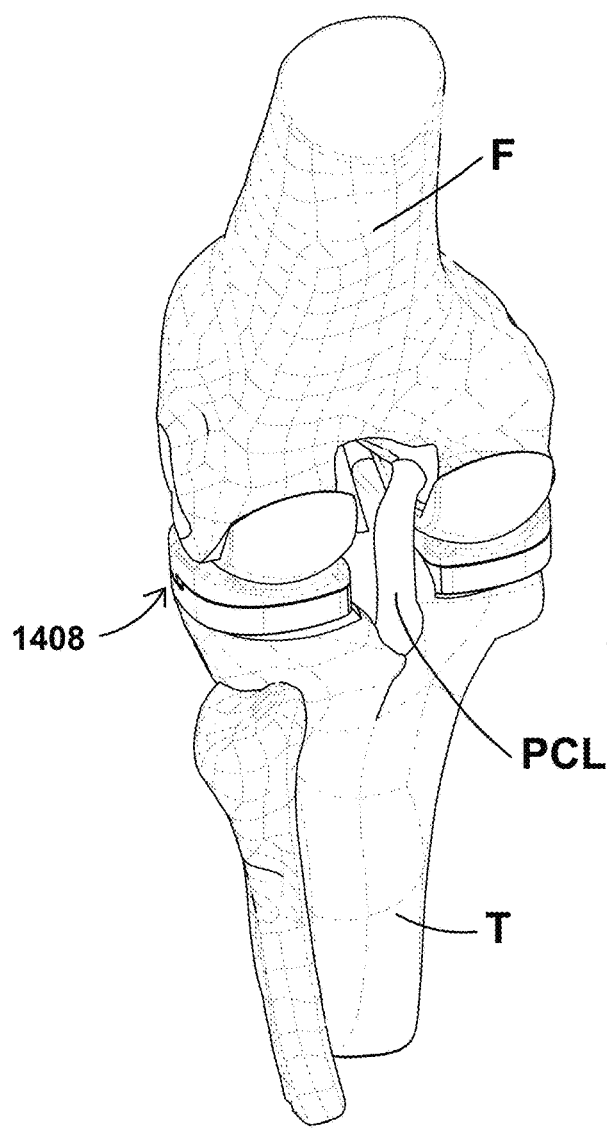
FIG. 69 is a schematic perspective view of a knee joint from a posterior aspect.
Figure 70:
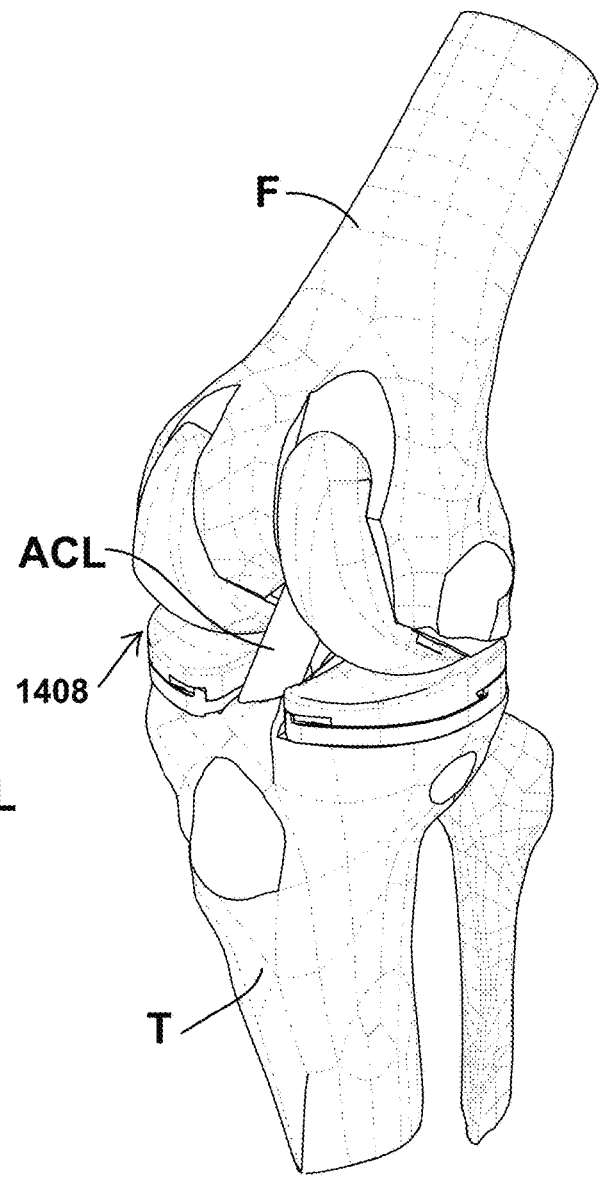
FIG. 70 is a schematic perspective view of a knee joint from an anterior aspect.

It is noted that many if not all of the embodiments of gap balancers described above do not require significant structural intrusion into the anterior or posterior aspects of the knee joint J. For example, they do not require bulky instrumentation or control connections. They are thus suitable for use within the knee joint J while preserving one or both of the cruciate ligaments of the joint J. FIGS. 69 and 70 illustrate the knee joint J with an endoprosthesis 1408 in place. It can be seen that the posterior cruciate ligament "PCL" (FIG. 69) and the anterior cruciate ligament "ACL" "FIG. 70) remain in position.

After the knee joint J is moved through some or all of its range of motion while collecting the above-noted data, this data may be stored as a basis of reference. It may then be used to for various purposes. Nonlimiting examples of uses for the data include: (1) mapping a surface profile or geometry of the formal condyle, i.e., producing a digital geometric model of the femoral condyle; (2) as a reference to determine the current position of the knee joint J without requiring reference to an external measurement device or pairs of trackers; (3) producing computed measurements of ligament tension which may be used in a soft-tissue balancing procedure.

Figure 71:
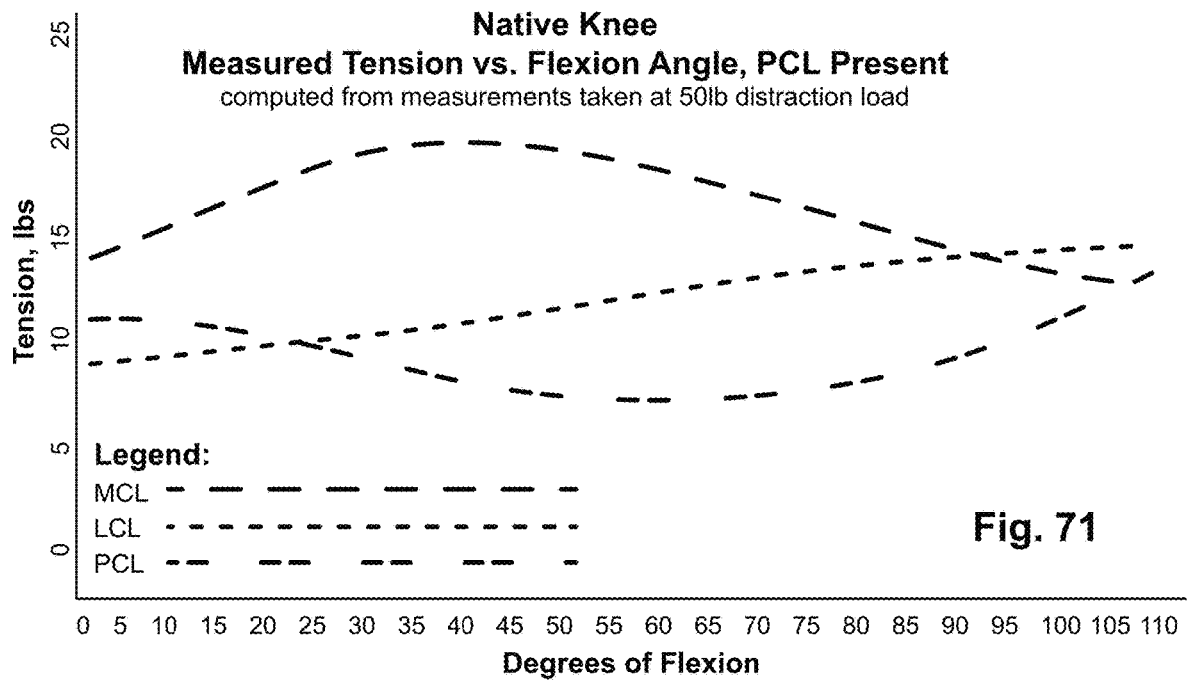
FIG. 71 is a graph of actual ligament tension versus knee joint flexion angle, in a native knee joint.
Figure 72:
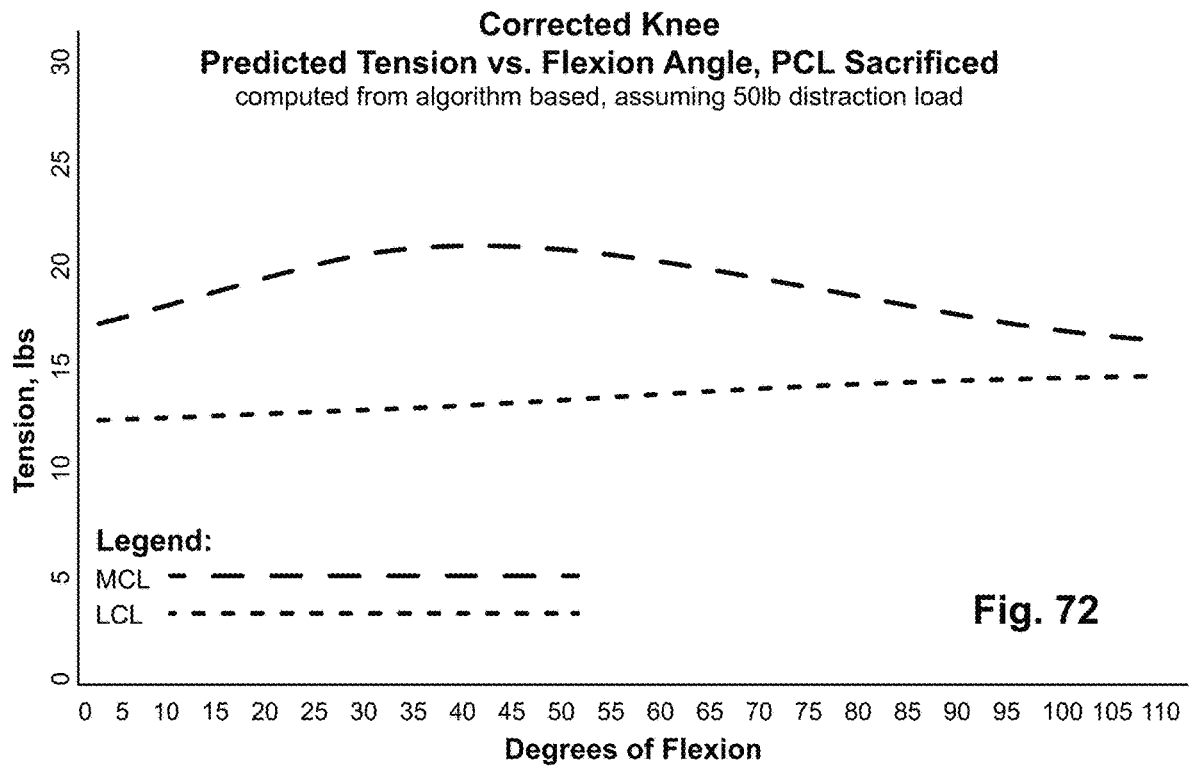
FIG. 72 is a graph of predicted ligament tension versus knee joint flexion angle, in a surgically corrected knee.

FIGS. 71 and 72 show example plots of how the sensor data could be used for a soft-tissue balancing procedure. FIG. 71 illustrates a graph of actual ligament tension versus knee joint flexion angle, in a native (i.e., preoperative) knee. The ligament tension values may be computed from measurements taken by the sensors described above, with a known distraction load (example: approximately 23 kg/50 lbs.). FIG. 72 illustrates a graph of predicted ligament tension versus knee joint flexion angle, in a surgically corrected knee. The ligament tension values are predicted based on a known distraction load (example: approximately 23 kg/50 lbs.).

Optionally, the sensor data may be compiled in a database and/or a learning system.

The gap balancer 10 is especially useful for adjusting the soft tissue lateral tension balance of a human knee joint. The coronal plane angle of the joint J (i.e., varus/valgus angulation) may be manipulated by selective augmentation and/ or release of the lateral collateral ligament or of the medial collateral ligament.

Various methods are known for augmentation of the soft tissues. As noted above, one method involves the use of an artificial tensile member such as a suture, cable, or filament, suitably anchored in tension. Examples of this type of device are illustrated in FIGS. 74-76.

Figure 74:
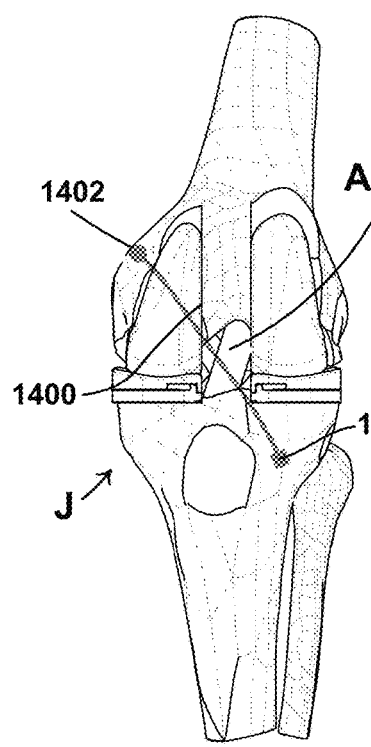
FIG. 74 illustrates a tensile member fixed by anchors and routed through the human knee joint across the anterior aspect of the joint.

FIG. 74 illustrates a tensile member 1400 fixed by anchors 1402 and routed through the human knee joint J across the anterior aspect of the joint J e.g., in order to replace or augment the anterior cruciate ligament ACL.

Figure 75:
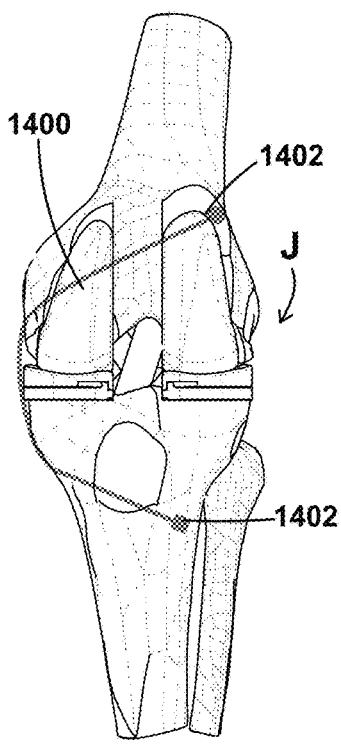
FIG. 75 illustrates a tensile member fixed by anchors and routed through the human knee joint across the medial aspect of the extension gap.

FIG. 75 illustrates a tensile member 1400 fixed by anchors 1402 and routed through the human knee joint J across the medial aspect of the extension gap e.g., in order to replace or augment the medial collateral ligament (not shown).

Figure 76:
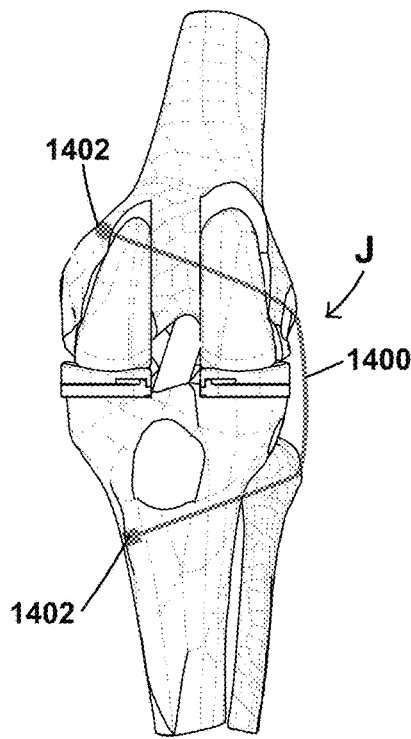
FIG. 76 illustrates a tensile member fixed by anchors and routed through the human knee joint across the lateral aspect of the extension gap.

FIG. 76 illustrates a tensile member 1400 fixed by anchors 1402 and routed through the human knee joint J across the lateral aspect of the extension gap e.g., in order to replace or augment the lateral collateral ligament (not shown).

Information provided by the gap balancer, the tracking markers, or combinations thereof may be used to facilitate various surgical procedures on the knee joint J.

Figure 73:
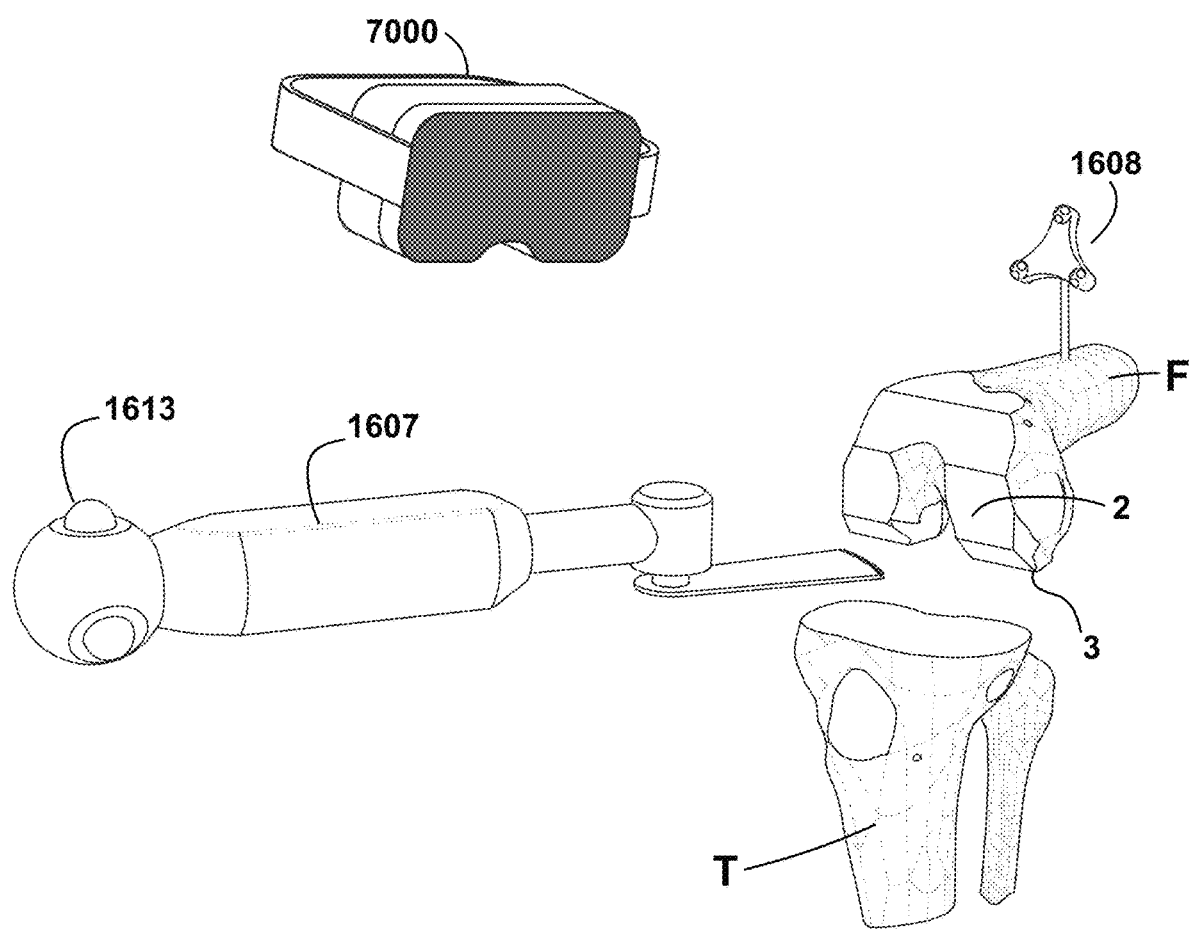
FIG. 73 is a perspective exploded view of the human knee joint in flexion, with a tracking marker attached to the femur, and a saw having another tracking marker being used to make one or more cuts on the joint.

For example, analysis of the sensor data may be used to compute a tool path such as a distal femoral cutting plane 2 or a posterior femoral cutting plane 3 (see FIG. 73).

Once the distal tool path determined, appropriate computations may be used to generate a definition of this cutting plane 2 relative to tracking marker 1608. The definition may include a set of coordinates lying on the cutting plane 2. Thus defined, the definition is then available so that a surgeon can make the distal femoral cut 2 (or another machined surface). In this context, the cutting plane 2 (or a portion thereof) defines a tool path. Alternatively, the cutting guidance (optionally along with other information, such as the virtual future position of the cuts and implants used) may be displayed on a body-worn display providing 2D or 3D graphics or providing a holographic heads-up display with an information panel (e.g., a Virtual Reality or augmented reality or mixed reality headset 7000).

In one example shown in FIG. 73, the tracking marker 1608 may be used to guide a bone saw 1607 to make the distal femoral cut 2 at appropriate angle and location. This guidance is possible because intercommunication between the bone saw 1607 (incorporating tracking marker 1613) and the tracking marker 1608 will give the relative position and orientation of the bone saw 1607 to that tracking marker. The cutting guidance may be provided in the form of information displayed on the remote display 1162 described above. For this purpose, 2-way data communications may be provided between and among the bone saw 1607 (or other surgical instrument), the tracking marker 1608, and the remote display 1162 or headset 7000.

Figure 78:
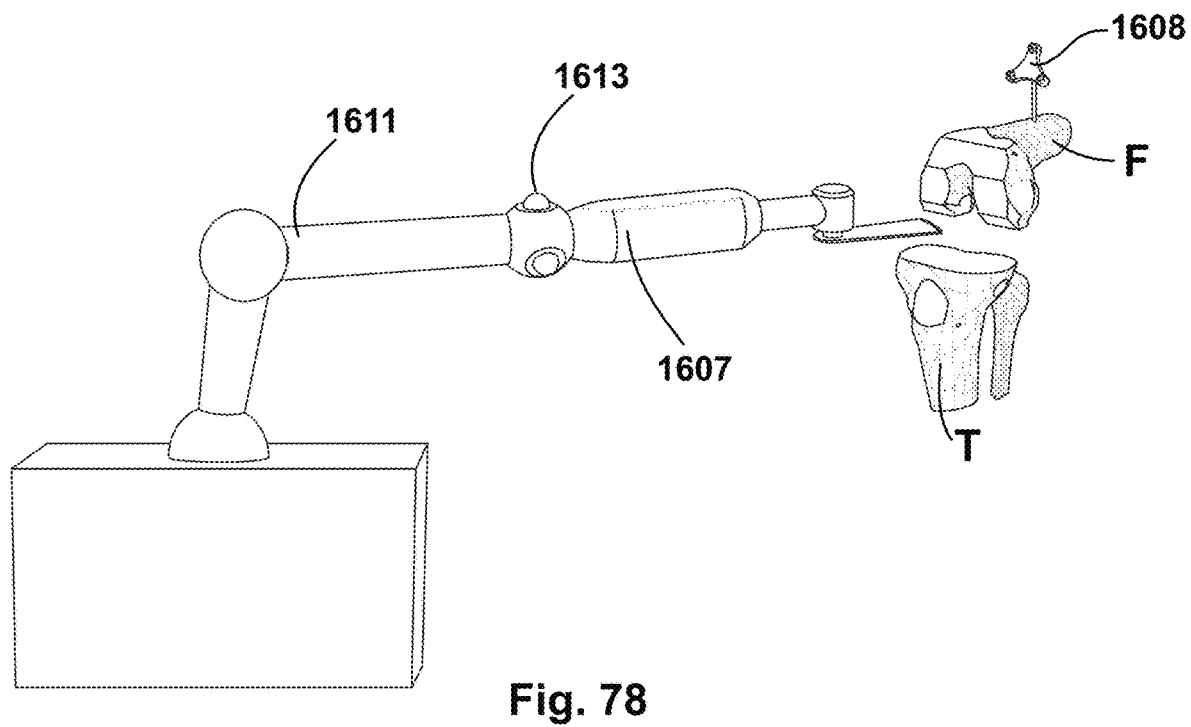
FIG. 78 is a perspective view of the human knee joint in flexion with a tracking marker attached to the femur, and a robot having a saw coupled thereto being used to make at least one cut on the knee joint.

Alternatively, the definition of the cutting plane 2 relative to tracking marker 1608 may be utilized to guide other equipment. For example, the definition may be provided to a surgical robot 1611 shown in FIG. 78 capable of manipulating a surgical tool such as a bone saw and moving the tool through a specified tool path.

Figure 77:
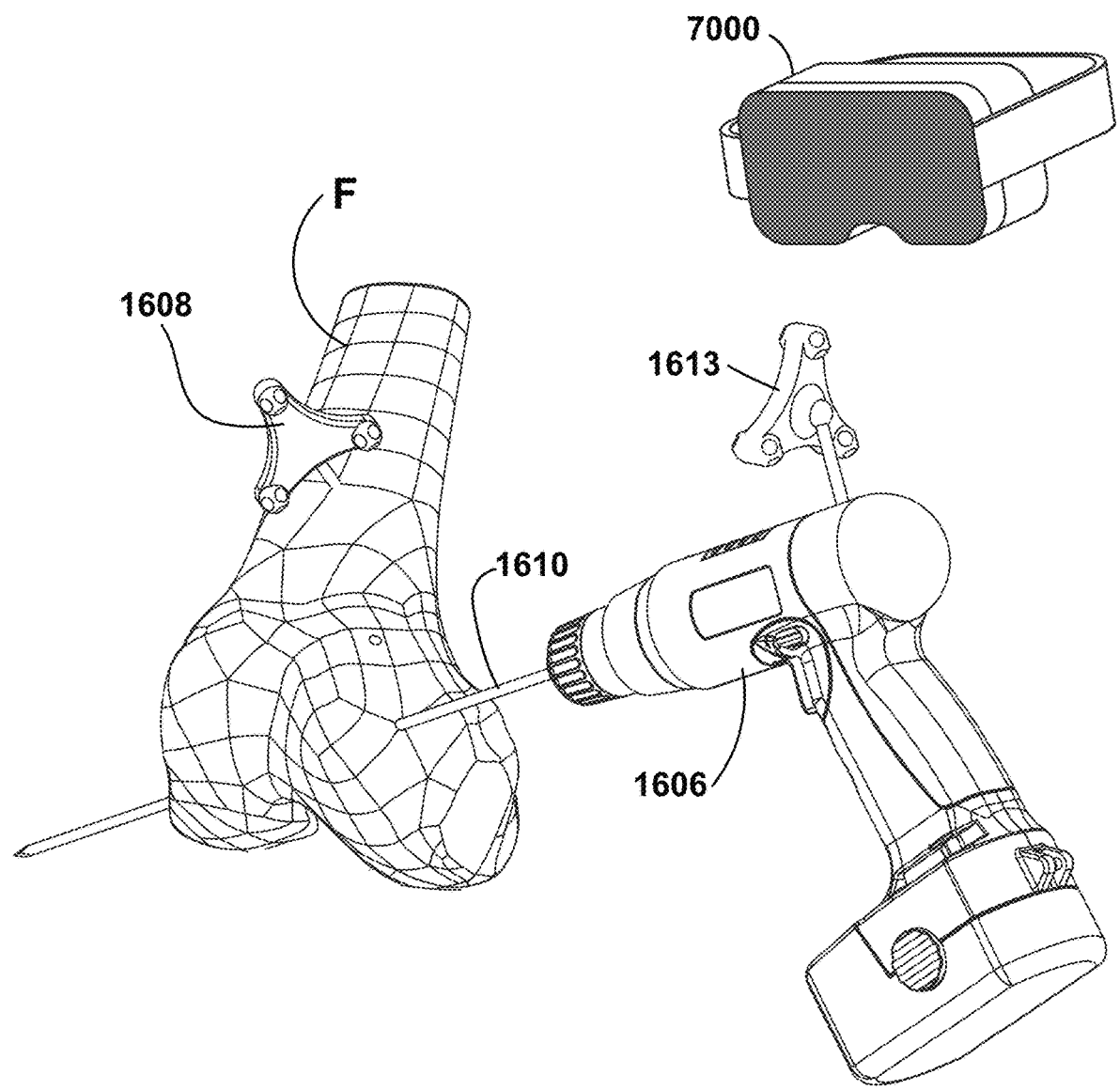
FIG. 77 is a perspective view of the human femur, with a tracking marker attached to the femur, and a drill having another tracking marker being used to form a hole in the femur.

As another example, analysis of the sensor data may be used to compute tool paths in the form of holes or channels for the passage and/or anchoring of tensile members is shown in FIG. 77, Once tool path is determined, the tracking markers 1602 and 1608 may be used to guide a cordless drill 1606 to drill a hole passing through the tool path, with the drill bit 1610 extending an appropriate angle. In this context, the hole to be drilled (or a portion thereof) defines a tool path. Guidance along the tool path is possible because intercommunication between the cordless drill 1606 (incorporating tracking marker 1613) and the tracking markers 1602 and 1608 will give the relative position and orientation of the cordless drill 1606 to those markers. The drilling guidance may be provided in the form of information displayed on the remote display 1162 described above. For this purpose, 2-way data communications may be provided between and among the cordless drill 1606 (or other surgical instrument), the tracking markers 1602 and 1608, the actuating instrument 1100, and the remote display 1162. It should be noted that the drill 1606 can be guided with reference to only a single tracking marker 1608 coupled to the femur F. Alternatively, the drilling guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 7000).

Figure 79:
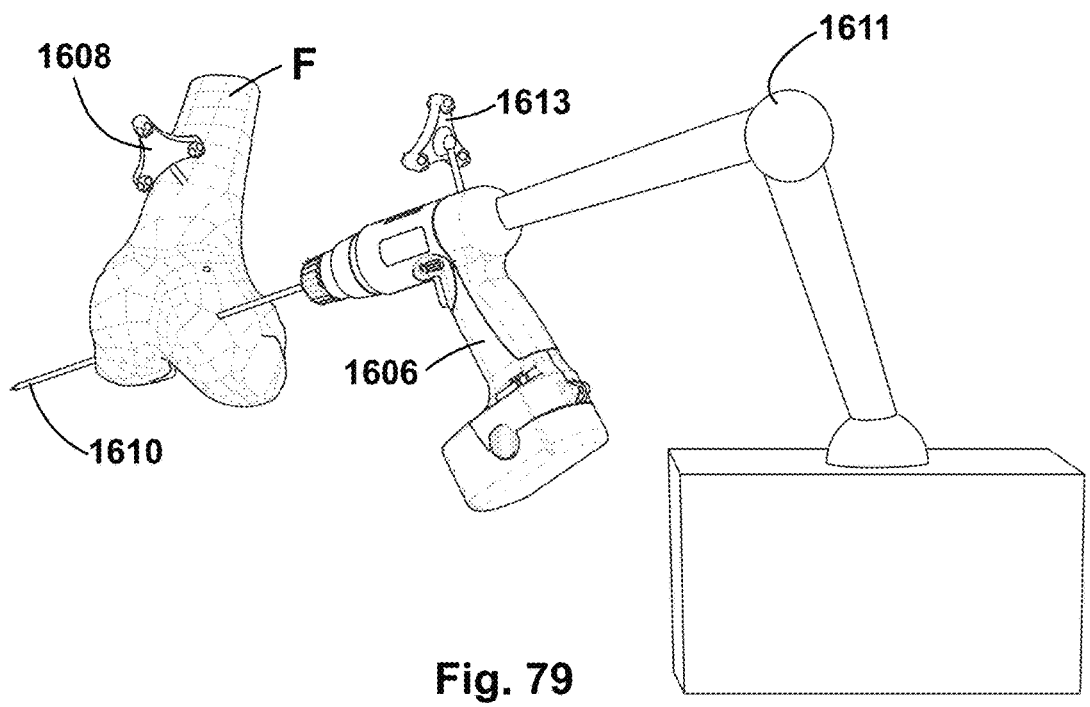
FIG. 79 is a perspective view of the human femur with a tracking marker attached thereto, and a robot having a drill coupled thereto being used to form a hole in the femur.

Alternatively, the definition of the tool path relative to tracking marker 1608 may be utilized to guide other equipment. For example, the definition may be provided to a surgical robot 1611 shown in FIG. 79 capable of manipulating a surgical tool such as a drill 1606 and moving the tool through a specified tool path.

This method is especially helpful in providing drilling guidance because it provides the benefits of a surgical navigation system, which is typically large, complex, and expensive, using simple inexpensive local relative position information. For example, the absolute position and orientation of the knee joint J is not required to perform the step of moving the joint J through the range of motion and then guiding the cordless drill 1606 to drill a hole at the appropriate location and orientation.

The apparatus and methods described herein are suitable for facilitating numerous types of surgical procedures on the knee, including soft tissue balancing as well as full knee replacement and intermediate procedures. The methods and apparatus described herein may be employed with varying levels of automation and using different specific processes. These may be described using four broad phases as follows:

Phase 1: pre-operative input. In this phase, the surgeon may gather information on the existing knee joint J using external physical measurements and/or medical imaging processes such as magnetic resonance imaging (MRI) or computerized axial tomography/computerized tomography (CAT/CT) scan.

Phase 2: intraoperative input. In this phase, data is collected from within the surgical field and/or the interior of the joint J. For example, data may be collected from the sensors described above.

Phase 3: interpretation. In this phase, appropriate software is used for modeling, algorithmic calculation for planning of tool paths, and/or corrective actions. This phase, in particular, can incorporate aspects of machine learning or learning systems. For example, data representing pre-operative anatomy and post-operative anatomy may be collected for multiple procedures. This data may be analyzed and used to improve subsequent procedures. For example, a learning system may be programmed to correlate a specific type of corrective cut or corrective tethering procedure with a specific knee pathology.

Learning system concepts may be applied to define and refine methods and techniques to train a learning system to analyze input information and parameters to produce a geometric treatment plan, via the native algorithm, and measure postoperative outcomes. Then feeding this information back into the learning system to further refine the system and algorithm to produce better patient outcomes. A multivariate model can be constructed to apply patient knee measurements such as ligament tension, laxity, and physical relationships, and bone geometry such as femoral condyle shape (medial and lateral) and flexion, extension, and full range geometry and ligament tension. To produce a defined geometric treatment regimen; bone resections, and in some cases ligament augmentation. In the case of ligament augmentation, geometric elements such as correct femoral epicondyle transosseous canal and corresponding tibial transosseous canal locations and positional relationships can be defined to produce improved ligament augmentation to correct knee motion.

Other techniques may be applied such as supervised, semi-supervised, and unsupervised learning system structures to improve patient outcomes for knee procedures, including but not limited to, uni- and total knee arthroplasty. Over time, a structured database may be built to continually refine outcomes based on a system that learns from preoperative, intraoperative (including measurement parameters and algorithmic operative execution), and postoperative imaging and physical follow up and measurement to continually improve functional geometric results and measured and declared patient satisfaction.

Using machine learning techniques permits the system to learn adaptively over accumulation of this data to assist predictive aspect of computational technology. Below are nonlimiting examples of information which could be gathered as inputs into the feedback system to iteratively make it a better predictive tool:
  a. Preoperative Assessment (x-ray, 3D scan/imaging/analysis)
  b. Intraoperative data and kinematics collected (these are the most objective and easiest to obtain):
    i. Ligament stress vs. strain curve (nonlinear) to gain knowledge of what is the "correct" distraction force to apply to differing anatomies and physiologies
    ii. Effects of ligament augmentation and tethering on knee kinematics and balance through ROM (range of motion)
    iii. Effects of shifting resection cut planes (normal translation and axial rotation) on knee kinematics and balance through ROM (range of motion)
    iv. Internal rotation of tibia that occurs with flexion (screw home, helical axis) and the effect of coronal plane on tibia axial movement
  c. Postoperative patient outcomes collected and analyzed. Including:
    i. Augmented ligament remodeling over time
    ii. Biological and Molecular level analysis
    iii. PROMS (patient reported outcomes measurements)

Phase 4: execution of corrective actions. In this phase, the surgical tools (e.g., saw, drill) are moved by one or more actuators (e.g., robotic actuators) under software control, or guidance is provided for surgical tool movement, or some combination thereof. As part of this phase, tool path guidance (optionally along with other information) may be displayed on one or more devices providing 2D or 3D graphics (e.g., a Virtual Reality or augmented reality or mixed reality headset 7000). Alternatively, or in addition to tool path guidance, the surgeon or other staff may be presented other information such as a 3D-modeled representation of the joint J with information overlaid on or combined therewith.

A high-level description of methods of using the gap balancer described herein, as specifically applied to the knee, is as follows:
  1. Map and Digitize the articular surfaces of the knee, using one of the gap balancer embodiments described above. This serves multiple functions:
    a. Establish key landmarks and anatomical elements to be used as datums
    b. Register the topography of the articular surfaces—for example:
      i. Femur: anterior, distal, posterior, anterolateral, anteromedial, posterolateral, posteromedial
      ii. Tibia: lateral meniscus, medial meniscus (from anterior horn to posterior horn of each)
      iii. Patella (optional): posterior surface and trochlear groove of femur
    c. Mapping the pathological articular surfaces is important for the following reasons:
      i. To quantify and visualize the bone that will be removed when corrective actions are carried out.
      ii. To locate the landmarks and anatomical features that will be referenced during computation and execution of corrective actions.

2. Quantify the tensile members under measured loading (induced by distraction of the knee joint, using one of the gap balancer embodiments capable of distraction, e.g. gap balancer 110 of FIG. 11, or measured manipulation of the knee joint using one of the gap balancer embodiments not capable of distraction, e.g., gap balancer 610 of FIG. 31):
   a. Primarily the quad mechanism: Lateral Collateral ligament (LCL), Medial Collateral ligament (MCL), Anterior Cruciate Ligament (ACL), Posterior Cruciate ligament (PCL).
   b. Secondarily the Patellar tendon, Quadriceps tendon, and the capsular tightness in general
   c. Quantifying the tensile members under measured loading is important for the following reasons:
      i. To understand the soft tissue issues that need to be addressed by the corrective actions that are planned.
      ii. To be confident in the distraction load(s) that need to be utilized during tensioned-measured balancing.
      iii. To be confident in the prescribed tightness of native and/or augmented ligaments in the final corrected knee.
3. Compute corrective actions to achieve desired implant positioning
   a. Considering the effects of:
      i. preservation vs. sacrifice of anatomical tensile elements.
      ii. Choice of implant, for example total knee or bicondylar unicompartmental knee.
      iii. 6 DOF implant positioning.
      iv. Augmentation and tethering.
   b. This computation is realized in the following manner:
      i. Final implants are positioned onto the digital 3D model of the pathological knee. This enables the corrective actions to be visualized:
         1. Resection planar locations and distances/amounts (which define implant position).
         2. Ligament augmentation osseous passage locations (entry & exit) and quantified tension. Tension is computed throughout range of motion and can also be visualized.
         3. Implant sizing.
         4. Implant type (posterior-stabilized, cruciate-retaining, etc.).
      ii. The above parameters can be adjusted from the initial computational output at the surgeon's discretion. The resulting kinematic alterations can be visualized virtually in real-time.
   4. Corrective actions may then be carried out by robot and/or by assistance of guided instrumentation, as described above.

The apparatus and method described herein have numerous advantages over prior art apparatus and techniques.

The gap balancer in some embodiments enables patella-in-place gap balancing during total knee arthroplasty. By allowing the patella (and other soft tissue around the knee space) to remain in its anatomical position during the balancing procedure, a more accurate and anatomically relevant gap can be established.

Furthermore, due to its non-intrusive nature, the gap balancer can enable in-situ gap balancing by means of soft tissue releases (to open one side of the gap relative to the other to make it more "rectangular" and less "trapezoidal") and tension ligament augmentation (to close one side of the gap by tightening or augmenting ligaments to make it more "rectangular" and less "trapezoidal").

The foregoing has described apparatus and methods for knee joint evaluation and treatment. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method of evaluating a human knee joint which includes a femur bone, a tibia bone, a patella bone, and ligaments, wherein the ligaments are under anatomical tension to connect the femur and tibia together, creating a load-bearing articulating joint, the method comprising:
   without making a tibial plateau cut, inserting into the knee joint a gap balancer that includes a tibial interface surface, an opposed femoral interface surface, and at least one force sensor, wherein the force sensor has at least a two-axis array resolution, with the gap balancer in a retracted position;
   moving the gap balancer towards an extended position, so as to urge the tibia and the femur apart and apply tension to ligaments of the knee joint;
   providing an electronic receiving device;
   moving the knee joint through at least a portion of its range of motion;
   while moving the knee joint, using the electronic receiving device to collect data from the at least one force sensor;
   processing the collected data to produce a digital geometric model of at least a portion of the knee joint; and
   storing the digital geometric model for further use.

2. The method of claim 1 wherein the data includes information from an array of tibial force sensors and an array of femoral force sensors.

3. The method of claim 1 wherein the gap balancer includes one or more individual devices, each one of the one or more individual devices placed in a single compartment of the knee joint.

4. The method of claim 1 further comprising:
   computing one or more tool paths passing through the knee joint;
   coupling at least one tracking marker to the knee joint;
   receiving data representing an actual position and orientation of a tool relative to the at least one tracking marker;
   moving a tool along the one or more tool paths, with reference to the data, so as to remove bone from the knee joint, thereby forming a machined feature in the knee joint.

5. The method of claim 1 wherein the two-axis array lies on a non-planar surface.

6. The method of claim 1 wherein the force sensor also produces position or displacement data.

7. The method of claim 6 further comprising force and displacement data being shown graphically to a user.

8. The method of claim 1 further comprising:
   connecting at least one position tracking sensor directly or indirectly to the knee joint;

collecting position data from the position tracking sensor while moving the knee joint; and, using the position data and the force data to produce the geometric model.

9. The method of claim 1 wherein the patella remains in its native anatomical position during all steps of the method.

10. The method of claim 1 wherein the data is compiled in a database and learning system.

* * * * *